United States Patent
Followill et al.

(10) Patent No.: US 11,986,326 B2
(45) Date of Patent: May 21, 2024

(54) COMPUTED TOMOGRAPHY (CT) IMAGING ARTIFACT REDUCTION TECHNIQUE MAKING USE OF TILTED SCANS

(71) Applicant: Board of Regents, The University of Texas System, Austin, TX (US)

(72) Inventors: David Followill, Houston, TX (US); Stephen Kry, Houston, TX (US); Daniela Branco, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 311 days.

(21) Appl. No.: 17/618,429

(22) PCT Filed: Jun. 10, 2020

(86) PCT No.: PCT/US2020/037095
§ 371 (c)(1),
(2) Date: Dec. 10, 2021

(87) PCT Pub. No.: WO2020/252094
PCT Pub. Date: Dec. 17, 2020

(65) Prior Publication Data
US 2022/0249033 A1 Aug. 11, 2022

Related U.S. Application Data

(60) Provisional application No. 62/860,052, filed on Jun. 11, 2019.

(51) Int. Cl.
*A61B 6/03* (2006.01)
*A61B 6/00* (2006.01)
*A61B 6/51* (2024.01)

(52) U.S. Cl.
CPC ............ *A61B 6/032* (2013.01); *A61B 6/51* (2024.01); *A61B 6/5241* (2013.01); *A61B 6/5282* (2013.01)

(58) Field of Classification Search
CPC ......... A61B 6/032; A61B 6/51; A61B 6/5241; A61B 6/5282; A61B 6/583; A61B 6/501; A61B 6/5205; A61B 6/5235; A61B 6/5258; G06T 5/77; G06T 5/94; G06T 2207/10081; G06T 2207/20221; G06T 2207/30036; G06T 5/50
See application file for complete search history.

(56) References Cited

U.S. PATENT DOCUMENTS

| | | |
|---|---|---|
| 6,229,869 B1 | 5/2001 | Hu |
| 6,831,961 B1 | 12/2004 | Tybinkowski et al. |
| 7,548,604 B2 | 6/2009 | De Man et al. |

(Continued)

OTHER PUBLICATIONS

Branco, D. et al., "Development of a stereoscopic CT metal artifact management algorithm using gantry angle tilts for head and neck patients," *J Appl Clin Med Phys*, (2020): 1-11.

(Continued)

*Primary Examiner* — Courtney D Thomas
(74) *Attorney, Agent, or Firm* — Parker Highlander PLLC

(57) ABSTRACT

Apparatus and methods for imaging a region of a subject comprising an artifact. In certain embodiments, the apparatus and methods utilize computed tomography (CT) scans obtained at two different angles to image a region posterior to an artifact.

10 Claims, 20 Drawing Sheets

(56) References Cited

U.S. PATENT DOCUMENTS

| | | |
|---|---|---|
| 7,818,045 B2 | 10/2010 | Rietzel |
| 8,244,016 B2 | 8/2012 | Medow |
| 8,254,518 B2 | 8/2012 | Paidi et al. |
| 8,396,275 B2 | 3/2013 | Bruder et al. |
| 8,891,847 B2 | 11/2014 | Helm et al. |
| 9,084,888 B2 | 7/2015 | Poulsen et al. |
| 9,437,018 B2 | 9/2016 | Dong et al. |
| 9,689,812 B2 | 6/2017 | Garms et al. |
| 10,147,207 B2 | 12/2018 | Chen et al. |
| 10,226,221 B2 | 3/2019 | Matthews |
| 10,265,044 B2 | 4/2019 | Profio et al. |
| 10,307,129 B2 | 6/2019 | Lee et al. |
| 2006/0020200 A1 | 1/2006 | Medow et al. |
| 2007/0083101 A1 | 4/2007 | Rietzel |
| 2008/0165920 A1* | 7/2008 | De Man ............... A61B 6/4447 382/131 |
| 2011/0081071 A1 | 4/2011 | Benson et al. |
| 2011/0298793 A1 | 12/2011 | Lauritsch et al. |
| 2012/0313943 A1 | 12/2012 | Tsukagoshi et al. |
| 2017/0238897 A1 | 8/2017 | Siewerdsen et al. |

OTHER PUBLICATIONS

Gjesteby, L. et al., "Metal Artifact Reduction in CT: Where Are We After Four Decades?," *IEEE Access*, 4 (2016): 5826-5849.

Huang, J. Y. et al., "An evaluation of three commercially available metal artifact reduction methods for CT imaging," *Physics in Medicine and Biology*, 60 (2015): 1047-1067.

Jun, K. et al., "Alignment Solution for CT Image Reconstruction using Fixed Point and Virtual Rotation Axis," *Scientific Reports*, 7 (2017): 1-11.

PCT Preliminary Report on Patentability issued in International Patent Application No. PCT/IS2020/037095, mailed Dec. 23, 2021.

PCT International Search Report and Written Opinion issued in International Patent Application No. PCT/US2020/037095, mailed Sep. 18, 2020.

Richard, P. et al., "Dental amalgam artifact: Adverse impact on tumor visualization and proton beam treatment planning in oral and oropharyngeal cancers," *Pract Radiat Oncol.*, 5 (2015): 583-588.

\* cited by examiner

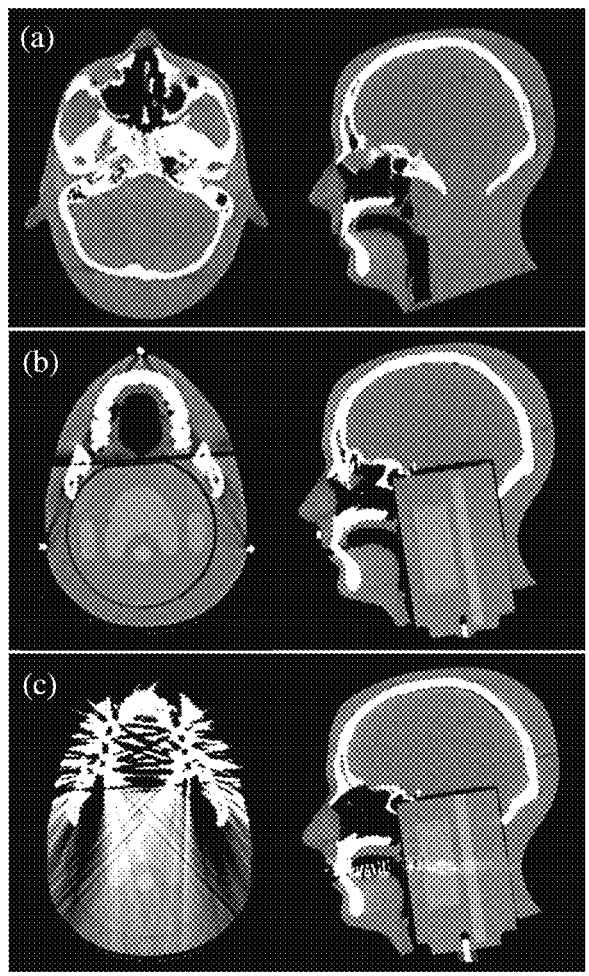
FIGS. 10A-C

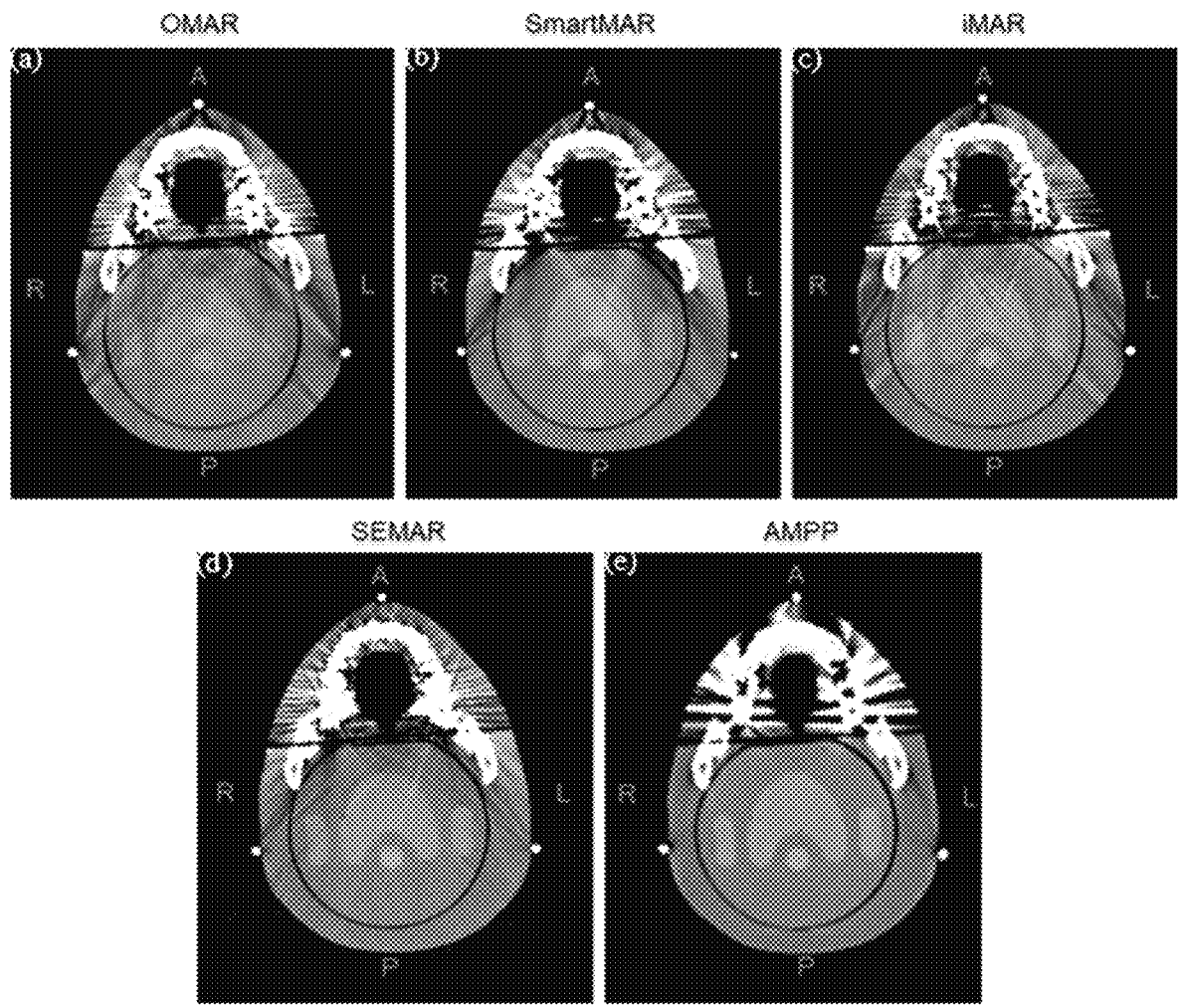
FIGS. 11A-E

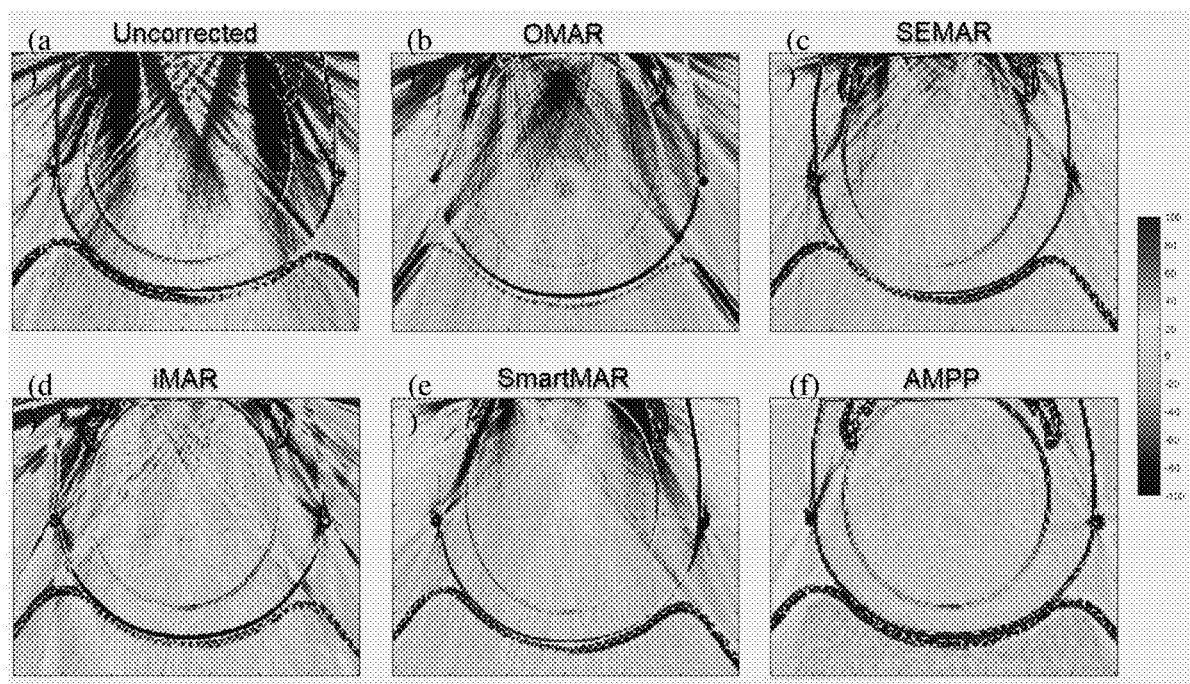
FIGS. 12A-F

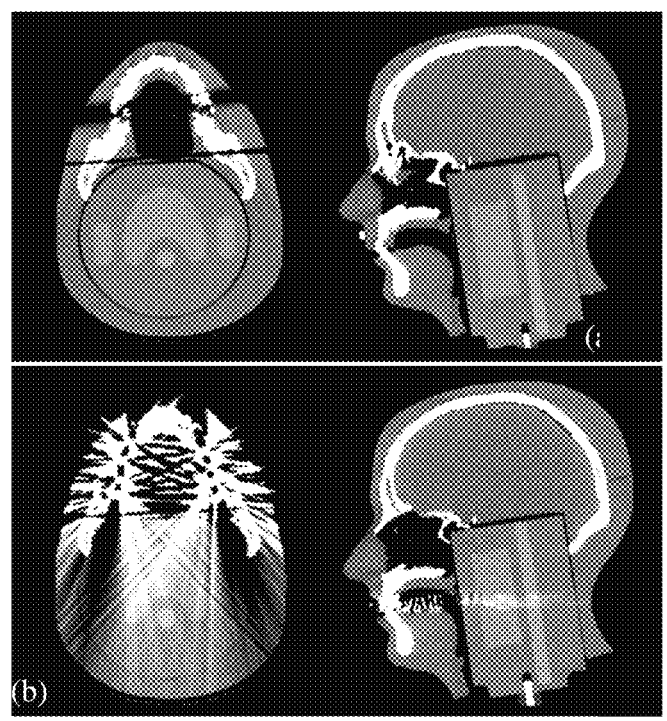
FIGS. 13A-B

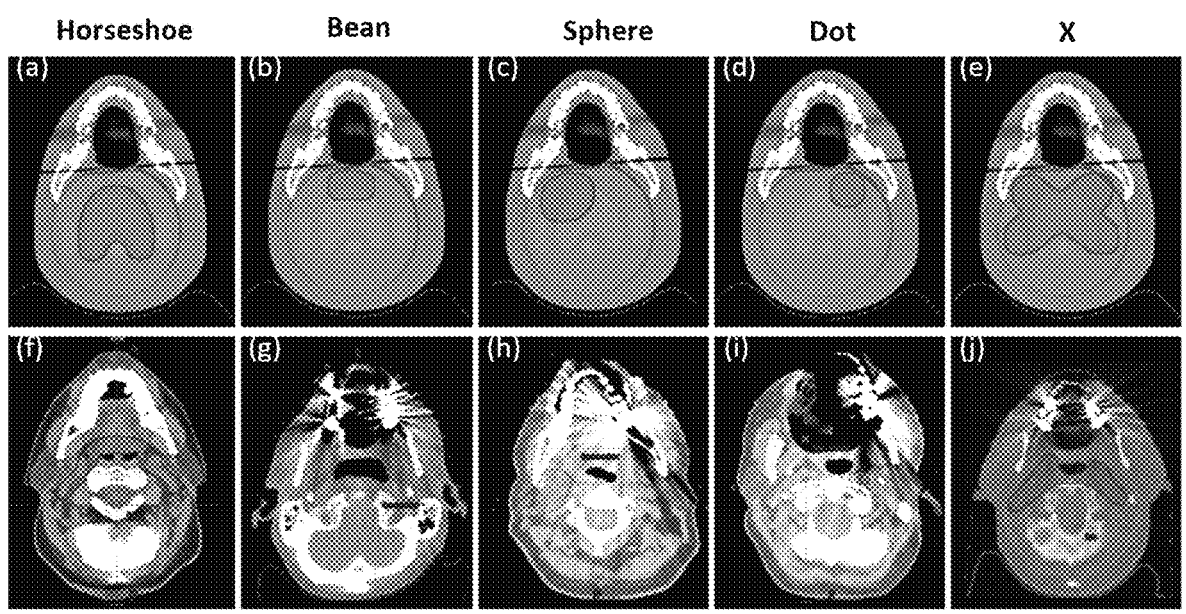
FIGS. 14A-J

|  | PTV D95 (%) |  | CTV D99 (%) |  | V100 (%) |  | D0.03cc (%) |  | Heterogeneity Index |
|---|---|---|---|---|---|---|---|---|---|
|  |  |  |  | Horseshoe Target |  |  |  |  |  |
| NoMAR | 100.2 | NoMAR | 99.4 | NoMAR | 96.0 | Baseline | 103.5 | Baseline | 1.027 |
| SEMAR | 100.3 | SEMAR | 99.8 | iMAR | 99.3 | SEMAR | 104.4 | AMPP | 1.032 |
| Baseline | 100.9 | iMAR | 100.2 | OMAR | 100.0 | AMPP | 104.8 | OMAR | 1.038 |
| iMAR | 101.0 | Baseline | 100.7 | SEMAR | 100.0 | iMAR | 105.2 | SEMAR | 1.040 |
| SmartMAR | 101.0 | AMPP | 100.8 | SmartMAR | 100.0 | OMAR | 105.6 | iMAR | 1.043 |
| AMPP | 101.1 | OMAR | 101.1 | Baseline | 100.0 | SmartMAR | 107.2 | SmartMAR | 1.045 |
| OMAR | 101.4 | SmartMAR | 101.7 | AMPP | 100.0 | NoMAR | 107.6 | NoMAR | 1.068 |
|  |  |  |  | Sphere Target |  |  |  |  |  |
| NoMAR | 99.1 | OMAR | 98.3 | OMAR | 79.9 | SmartMAR | 104.8 | Baseline | 1.050 |
| OMAR | 99.1 | NoMAR | 98.6 | iMAR | 86.0 | OMAR | 105.2 | AMPP | 1.050 |
| iMAR | 99.4 | iMAR | 98.7 | SmartMAR | 88.8 | iMAR | 105.3 | SmartMAR | 1.059 |
| SEMAR | 99.9 | SmartMAR | 98.8 | NoMAR | 91.6 | AMPP | 105.3 | SEMAR | 1.060 |
| SmartMAR | 99.9 | SEMAR | 99.5 | SEMAR | 95.9 | Baseline | 105.4 | iMAR | 1.064 |
| Baseline | 100.4 | AMPP | 100.1 | Baseline | 99.7 | NoMAR | 105.5 | OMAR | 1.066 |
| AMPP | 100.4 | Baseline | 100.2 | AMPP | 99.7 | SEMAR | 105.7 | NoMAR | 1.068 |
|  |  |  |  | Bean Target |  |  |  |  |  |
| iMAR | 98.5 | iMAR | 96.8 | iMAR | 88.3 | AMPP | 103.5 | Baseline | 1.031 |
| OMAR | 99.4 | OMAR | 98.6 | OMAR | 90.7 | Baseline | 104 | AMPP | 1.035 |
| AMPP | 100.4 | AMPP | 100.1 | AMPP | 99.5 | OMAR | 106.7 | NoMAR | 1.056 |
| Baseline | 101.0 | Baseline | 100.9 | Baseline | 100.0 | NoMAR | 107.5 | SEMAR | 1.072 |
| NoMAR | 102.0 | NoMAR | 101.5 | NoMAR | 100.0 | SmartMAR | 110.5 | OMAR | 1.079 |
| SmartMAR | 103.0 | SmartMAR | 102.1 | SEMAR | 100.0 | iMAR | 111 | SmartMAR | 1.082 |
| SEMAR | 103.9 | SEMAR | 103.5 | SmartMAR | 100.0 | SEMAR | 111.1 | iMAR | 1.146 |
|  |  |  |  | Dot Target |  |  |  |  |  |
| NoMAR | 99.5 | NoMAR | 100.0 | NoMAR | 99 | AMPP | 103.5 | Baseline | 1.023 |
| AMPP | 100.4 | AMPP | 100.8 | OMAR | 100 | Baseline | 103.7 | AMPP | 1.027 |
| Baseline | 100.8 | Baseline | 101.4 | SEMAR | 100 | NoMAR | 107.5 | SmartMAR | 1.035 |
| OMAR | 102.0 | OMAR | 101.9 | iMAR | 100 | OMAR | 108.5 | SEMAR | 1.047 |
| SEMAR | 104.5 | iMAR | 104.3 | SmartMAR | 100 | SEMAR | 109.5 | iMAR | 1.062 |
| iMAR | 104.6 | SEMAR | 104.6 | Baseline | 100 | SmartMAR | 109.5 | NoMAR | 1.075 |
| SmartMAR | 106.0 | SmartMAR | 105.9 | AMPP | 100 | iMAR | 110.8 | OMAR | 1.076 |
|  |  |  |  | X Target |  |  |  |  |  |
| NoMAR | 99.1 | NoMAR | 99.2 | NoMAR | 94.8 | Baseline | 105 | Baseline | 1.043 |
| SEMAR | 99.4 | OMAR | 99.4 | OMAR | 96.0 | NoMAR | 105.5 | AMPP | 1.045 |
| OMAR | 99.6 | SEMAR | 99.4 | SEMAR | 96.8 | SmartMAR | 105.5 | SmartMAR | 1.050 |
| iMAR | 100.0 | SmartMAR | 99.4 | iMAR | 97.4 | iMAR | 105.7 | iMAR | 1.054 |
| SmartMAR | 100.0 | iMAR | 99.6 | SmartMAR | 97.5 | AMPP | 105.8 | NoMAR | 1.055 |
| Baseline | 100.3 | Baseline | 100.2 | Baseline | 99.7 | OMAR | 106 | SEMAR | 1.057 |
| AMPP | 100.5 | AMPP | 100.3 | AMPP | 99.8 | SEMAR | 106 | OMAR | 1.059 |

FIG. 19

COMPUTED TOMOGRAPHY (CT) IMAGING ARTIFACT REDUCTION TECHNIQUE MAKING USE OF TILTED SCANS

CROSS-REFERENCE TO RELATED APPLICATIONS

This application is a national phase application under 35 U.S.C. § 371 of International Application No. PCT/US2020/037095, filed Jun. 10, 2020, which claims priority to U.S. Provisional Patent Application Ser. No. 62/860,052, filed Jun. 11, 2019, the entire contents of each of which are incorporated herein by reference.

BACKGROUND INFORMATION

Dental amalgams (high Z/density materials) are common sources of artifacts in Head and Neck (HN) images. Computed tomography (CT) imaging artifacts, i.e., discrepancies between true and displayed Hounsfield Unit (HU) values, can pose a problem for physicians when completing a diagnosis or attempting to identify or delineate the extent of disease. Dense objects, such as bone and metal, are a common source of artifacts in the reconstruction of the CT images through beam hardening and x-ray starvation. Beam hardening is caused by the presence of dense (and high atomic number) structures in the beam path. The x-ray spectrum undergoes an upward shift in average energy due to the lower energy photons being preferentially attenuated. CT reconstruction algorithms attempt to correct for beam hardening but are optimized for human tissues and cannot fully address highly attenuating materials such as metals [1]. Photon starvation occurs when these highly attenuating materials cause the exiting x-rays to have a low photon flux on the detectors. Consequently, the combination of beam hardening and photon starvation produce streaking artifacts in the reconstruction and can affect the image severely.

The most common artifacts present in head and neck (HN) cases are the ones caused by the presence of high atomic number materials in the image, such as dental amalgams. Dental filling metal amalgam artifacts can obscure the visualization of tumors in the oral cavity and oropharynx. This obscuring of the anatomy can lead to poor visualization of tissues and therefore improper definition of the target, potentially providing suboptimal management of the disease, particularly including radiotherapy quality. Studies have shown that the presence of dental artifacts can in fact increase the inter-observer contouring variability of HN tumors [2]. Aside from the difficulty in visualization of tumors and in definition of planning target volumes (PTVs) and organs and risk (OARs), metal artifacts will alter the true Hounsfield units (HU) in the affected voxels which negatively affects the quality of radiotherapy in such areas. Kim et al. and Mail et al. have demonstrated that such artifacts result in increased dose heterogeneity and reduced target coverage [3, 4]. In photon therapy, calculation errors can be as high as 12% when fillings are present, compared to 3% when no metal is present [5]. The consequences in proton dose calculations can be dramatically worse due the rigorous dependence between accurate representation of HU values and the correct relative linear stopping power prediction [6]. Proton treatment plans could display erroneous beam ranges and dose distributions when artifacts are present.

Current common practice to help manage metal artifacts includes the use of overriding techniques and of various metal artifact reduction algorithms. Overriding HU for known or expected values in CT images is both time-consuming and subjective, factors which can be eliminated with automated approaches such as available algorithms. However, a recent study focusing on three current commercially available artifact reduction methods concluded that they were generally not successful at reducing artifacts specifically caused by dental fillings [7]. Other post processing metal artifact reduction algorithms have been published but have not found clinical acceptance [8-10]. Other several solutions for metal artifact reduction have been proposed, but many are impractical or not clinically available and therefore are not extensively adopted. Newhauser et al. investigated streak related range errors and whether they could be avoided using mega voltage (MV) CT images in the proton treatment planning. They accomplished a significant range uncertainty improvement, from 5-12 mm using uncorrected kVCT to less than 3 mm using MVCT. However, it is not known whether MVCT images can be used in treatment planning. Hence, using a combination of kVCT, for better image quality, and MVCT, for reduced proton range error, was the optimal approach suggested in their study [11]. However, this study was only performed for proton delivery of the pelvis area and has not been evaluated for other disease sites. Further investigations are needed to determine the suitability of their approach for clinical use in the HN region. Replacing the metal amalgam with a radiologically inert composite material is also an available option. Composite fillings have been shown to demonstrate comparable HU ranges relative to native teeth [12]. Nonetheless, filling replacements can take approximately 1 hour per tooth and the cost and insurance coverage are not exactly determined. Hence, replacing fillings may seem relatively simple, but it requires additional time for dentist visits and may be inconvenient or costly for some patients.

Despite several publications of metal artifact reduction algorithms over the last two decades, there is still an evident need for better metal artifact management in highly heterogeneous sites, such as HN. A vast majority of commercial artifact reduction algorithms are based on the subtraction of metal data points from a thresholded sinogram (metal only), followed by the interpolation and replacement of the missing data by estimated (and not necessarily correct) data, possibly causing additional artifacts [13]. The artifact management algorithm developed in this work will not be based on direct interpolation methods and therefore will not require the removal, replacement and consequential loss of data points and, in addition, will not be system specific and thus will be available for any CT scanner that allows for gantry tilts. In this work, we will introduce the algorithm and provide initial testing on a geometrical phantom as a proof of principle.

Accordingly, a need exists for devices and methods that address the shortcomings in current apparatus and techniques for artifact reduction in CT scanning.

SUMMARY

As explained in more detail below, exemplary embodiments of the present disclosure enable improvements in many aspects of artifact reduction in CT scanning techniques and apparatus.

As disclosed herein, a metal artifact management algorithm was developed using CT gantry angle tilts and evaluated in a geometrical HN phantom. The embodiments disclosed herein offer the improvement of not requiring the replacement of deleted metal thresholded data with artificially/interpolated data. In exemplary embodiments, the algorithm developed herein used accurate HU data obtained from 2 different scans and was divided into 2 parts; the first of which included the untilting and correction of the angled image set, and the second the artifact removal portion. Unlike other existing algorithms, this algorithm is independent of the CT scanner provider and therefore can be used in any CT scanner that allows for gantry tilts. The images showed the successful removal of the artifacts present in the posterior region on the phantom, allowing for much better visualization of the structures. One potential issue with this technique is the introduction of artifacts to the nose and chin regions. However, those areas do not contain disease or OARs and do not normally have radiation treatment beams traversing them. The algorithm evaluation showed that the measured geometrical distortion and changes in HU accuracy were very small and had no statistically significant relationship with gantry angle. The HU accuracy measurements were found to be significantly similar to the baseline measurement and not related to gantry angle.

This technique ha two important limitations to be addressed, the first was related to patient size and the second to the extra dose delivered to the patient. Large sized patients can restrict the use of the largest available gantry angles, but while partially limiting the success of the artifact removal algorithm, it can still provide substantial benefit. Another issue to be considered is the extra dose delivered to the patient. However, the benefit obtained in the diagnostic and therapeutic settings outweighs the cost of the extra amount of dose delivered. Better visualization of tissues and disease and quality radiation dose calculations can provide a more positive impact to patients than the possible negatives from the negligible dose delivered from an extra CT scan. As shown in Example 2, treatment planning dosimetry was evaluated, specifically as applied to proton therapy since proton treatment quality and robustness are highly dependent on HU accuracy.

Commercial artifact reduction techniques have been offered, but many are impractical, produce inaccurate CT images or are not clinically available, thus not widely implemented. Embodiments disclosed herein use CT gantry tilts to develop a HN metal artifact management algorithm and investigate its improvement in proton treatment planning. In certain embodiments, the algorithm uses two angled CT scans in order to generate a single image set with minimal artifacts posterior to the metal implants. The algorithm was evaluated (geometrical distortion and HU accuracy) using a geometrical phantom simulating a HN patient with dental fillings. The phantom was jaw shaped containing teeth structures and plugs located posteriorly. The axial and sagittal views of the phantom at the same slice location at 0° without metal, 0° with metal and 30° CT tilt with metal after the algorithm showed significant improvement after the algorithm was used to manage the artifacts in the posterior region of the phantom. The integrity of the algorithm was studied based on distortion and HU accuracy, and the average total distortion for all gantry angles in the AP, LR and Z directions was 0.17 mm, 0.12 mm and 0.14 mm, respectively. The HU measurements showed significant consistency throughout the different reconstructed images when compared to the baseline image sets. Treatment planning comparisons will be performed (proton beam range differences, gamma analysis and general plan quality) between baseline and artifact corrected image sets.

Exemplary embodiments of the present disclosure include a method of imaging a region of a subject comprising an artifact, where the method comprises: obtaining a first computed tomography (CT) scan of the region, wherein the first CT scan comprises a first set of images obtained at a superior angle with respect to the subject; obtaining a second CT scan of the region, wherein the second CT scan comprises a second set of images obtained at an inferior angle with respect to the subject; performing a first three-dimensional affine geometric transformation to the first set of images and to the second set of images; performing a second three-dimensional affine geometric transformation to the first set of images and to the second set of images; converting the first set of images to a first modified set of axial images, wherein a first portion of the first modified set of axial images comprises a first artifact-free region posterior to the artifact; converting the second set of images to a second modified set of axial images, wherein a second portion of the second modified set of axial images comprises a second artifact-free region posterior to the artifact; and constructing an image of a region posterior to the artifact by combining the first artifact-free region posterior to the artifact and the second artifact-free region posterior to the artifact.

In particular embodiments, the first three-dimensional affine geometric transformation is a shear transformation applied on a sagittal plane of the first set of images and the second set of images. In some embodiments, the second three-dimensional affine geometric transformation is geometrical correction transformation of the first set of images and the second set of images. In specific embodiments, the first CT scan and the second CT scan are obtained by tilting a gantry of a CT scanner.

In certain embodiments, constructing the image of the region posterior to the artifact comprises combining the first artifact-free region posterior to the artifact and the second artifact-free region posterior to the artifact comprises analyzing pixels in the first modified set of axial images for a threshold Hounsfield Unit (HU) value. In particular embodiments, constructing the image of the region posterior to the artifact comprises combining the first artifact-free region posterior to the artifact and the second artifact-free region posterior to the artifact comprises analyzing pixels in the second modified set of axial images for the threshold HU value. In specific embodiments, the threshold HU value is equivalent to an HU value for a metal. In some embodiments, the metal is an amalgam dental filling, and in particular embodiments the metal is stainless steel.

Certain embodiments include an apparatus for imaging a region of a subject comprising an artifact, where the apparatus comprises: a computed tomography (CT) scanner comprising support surface and a tiltable gantry, wherein the CT scanner is configured to obtain CT scans at a superior and an inferior angle to the support surface; a computer processor; and a computer-readable medium which comprises instructions that when executed by the computer processor will cause the apparatus to perform the following steps:obtain a first CT scan of a region of a subject comprising an artifact, wherein the first CT scan comprises a first set of images obtained at a superior angle with respect to the subject; obtain a second CT scan of the region, wherein the second CT scan comprises a second set of images obtained at an inferior angle with respect to the subject; perform a first three-dimensional affine geometric transformation to the first set of images and to the second set of images; perform a second three-dimensional affine geometric transformation to the first set of images and to the second set of images; convert the first set of images to a first modified set of axial images, wherein a first portion of the first modified set of axial images comprises a first artifact-free region posterior to the artifact; convert the second set of images to a second modified set of axial images, wherein a second portion of the second modified set of axial images comprises a second artifact-free region posterior to the artifact; and construct an image of a region posterior to the artifact by combining the first artifact-free region posterior to the artifact and the second artifact-free region posterior to the artifact.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "substantially" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

FIGS. 10A-C display (A) axial and sagittal CT views of the Alderson phantom prior to modifications; (b) axial and sagittal CT views of the modified phantom, which included a cylindrical insert containing a central target and 3 healthy structures, and a jaw insert; and (c) axial and sagittal CT views of the modified phantom with metal amalgam capsules in the tooth holes. The metal artifacts generated by the capsules are evident FIGS. 11A-E display (a-e) axial and sagittal CT views of the anthropomorphic phantom, corrected using the commercial MAR algorithms (a-d) or the in-house-developed AMPP algorithm (e).

FIGS. 12A-F display HU error maps show differences between corrected images and corresponding baseline images, with severe HU differences are displayed by the dark red and dark blue colors.

FIGS. 13A-B display (a) axial and sagittal CT views of the modified Alderson phantom, including the jaw insert and the cylindrical insert (containing a central target, parotids, and spinal cord); and (b) Axial and sagittal CT views of the modified phantom with metal amalgam capsules in the tooth holes showing the metal artifacts that were generated.

FIGS. 14A-J display target contours created on the anthropomorphic phantom (a-e) were designed on the basis of a real HN patient (f-j), respectively.

FIG. 19 displays planning evaluation metrics for included targets.

DETAILED DESCRIPTION OF ILLUSTRATIVE EMBODIMENTS

Figure 1:
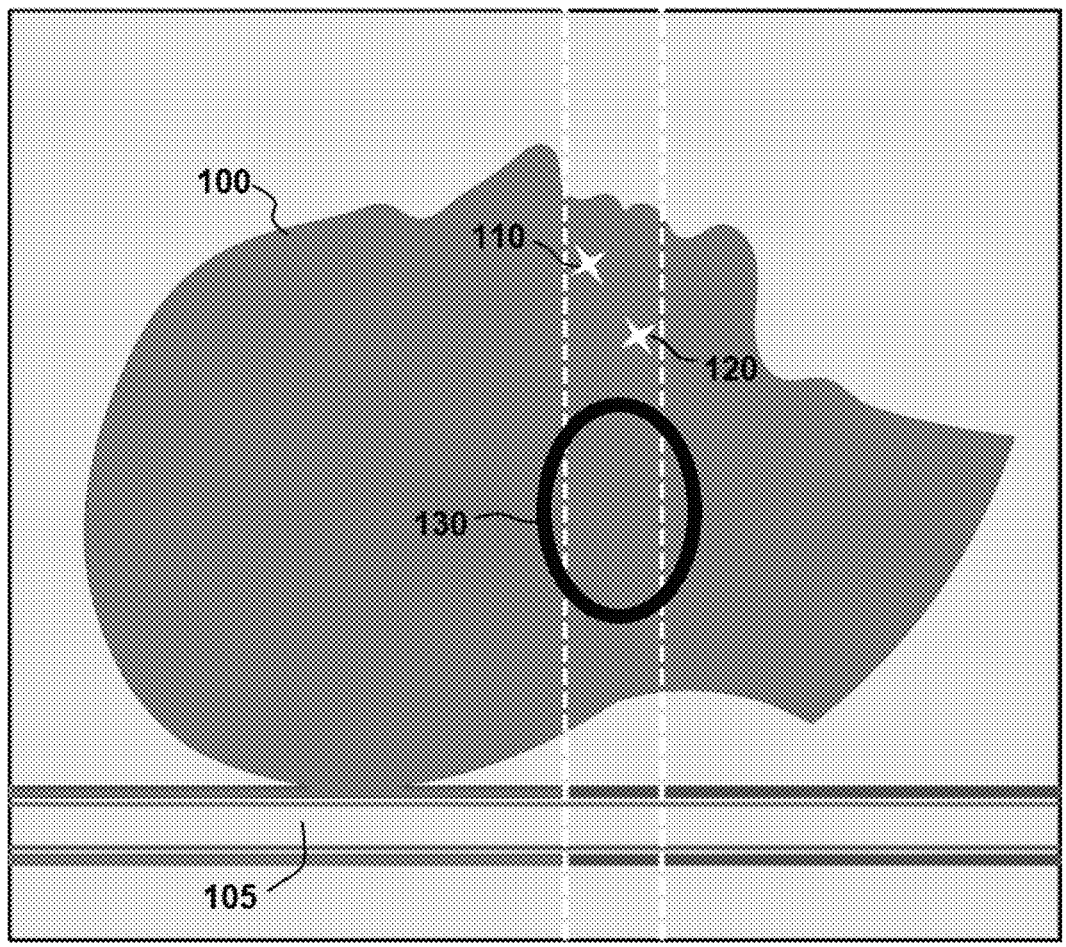
FIG. 1 displays a diagram representing a HN patient with the range of CT slices affected by the dental work.

As discussed more fully below, exemplary embodiments of the present disclosure include devices and methods for CT scans with reduced artifact effects. Particular embodiments include an algorithm that makes use of 2 angled CT scans in order to generate one artifact reduced image set. One issue with traditional 0 degree scans (e.g. scans performed in a plane perpendicular to a support surface supporting the subject) on HN patients with dental work is that the artifact compromised slices are located where typical HN disease is located (as shown in FIG. 1), posterior to the oral cavity. FIG. 1 shows a diagram representing subject 100 (e.g. a HN patient) on a support surface 105 with the range of CT slices affected by the dental work indicated by artifacts 110 and 120. A region 130 posterior to artifacts 110 and 120 (indicated with a black oval). Region 130 shows the region of typical HN disease that gets affected by metal artifacts present in the mouth.

Exemplary embodiments of the present disclosure use two (2) angled CT scans to reconstruct an image where posterior region 130 can display the accurate HU information, without the need for the widely used metal sinogram thresholding and interpolation techniques. In simple terms, the reconstruction technique is performed in the image space and is based on the combination of the superior portion of a superiorly titled scan 140 with the inferior portion of an inferiorly tilted or angled scan 150, as shown in the diagram in FIG. 2.

Figure 2:
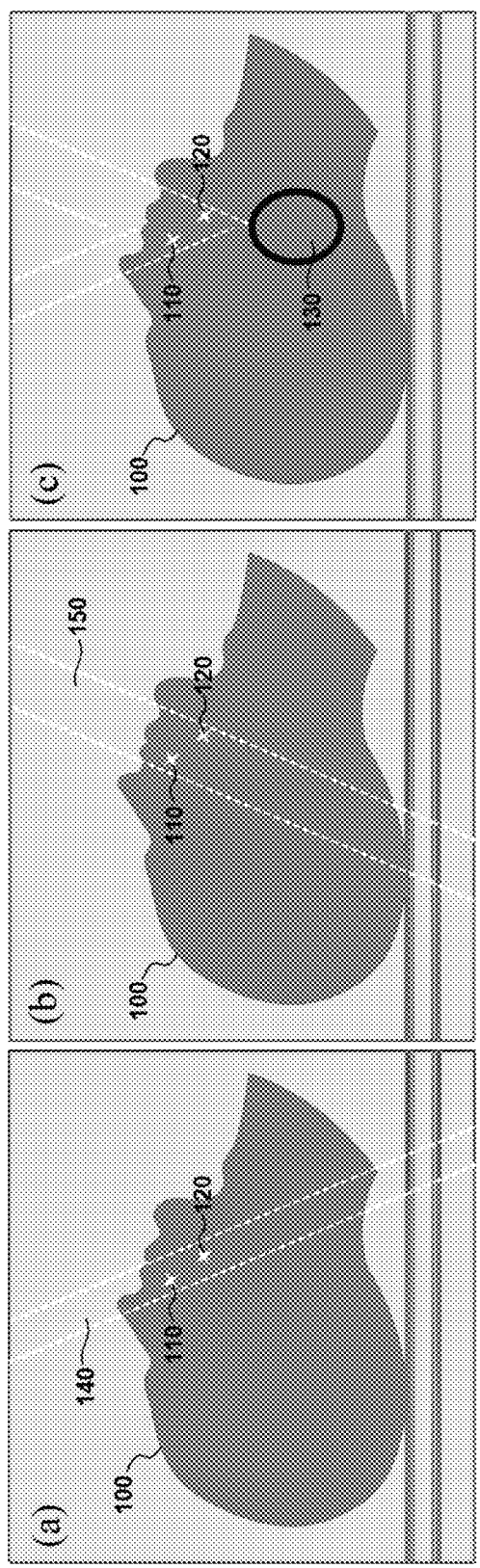
FIGS. 2A-C display a diagram of a sagittal view of a HN patient with the CT gantry tilted superiorly and inferiorly, along with the final artifact reduced image.

The imaging technique and reconstruction algorithm create an image with the actual HU information (not interpolated) present in the posterior region of the patient. In order to remove the artifacts from posterior region 130, they have to be focused on the anterior portion of the head, appearing in areas that were unaffected previous to the reconstitution, such as the nose and chin (FIG. 2, panel (c)). This compromise was found to be acceptable due to the fact that disease (and OARs) are not are located in those regions and vast majority of treatment plans avoid beam arrangements that traverse those anterior areas. FIG. 2 illustrates a diagram of a sagittal view of a HN patient with the CT gantry tilted superiorly (a) and inferiorly (b) showing the artifact affected slices. FIG. 2 panel (c) shows the final artifact reduced image with the posterior region clear and the artifacts focused on the anterior region.

The framework for the developed algorithm is divided into two main steps. The first step is responsible for untilting the images that were acquired at an angle, so that they appear as regular axial slices and can then be used in step 2. Step 2 uses those untilted images to form an image with the metal artifacts greatly reduced. The complete artifact reduction routine is dependent on the number of images per scan, but on average takes less than 1 minute to complete.

Step 1: Untilting of Image Set

This first step was accomplished by performing 3-D affine geometric transformations to the entire image volume. Affine transformations are done using linear mapping functions that preserve specific points, straight lines and planes. After affine transformations, sets of parallel lines remain parallel, making them suitable for this part of the algorithm. In order to achieve that, the algorithm performed a matrix multiplication with specific shear factors that were previously determined based on the angle of tilt of the gantry. The general form of this transformation is given by:

$$I = M \times I', \text{ where,}$$

$$I = \begin{bmatrix} x \\ y \\ z \\ 1 \end{bmatrix}, M = \begin{bmatrix} 1 & sh_{yx} & sh_{zx} & 0 \\ sh_{xy} & 1 & sh_{zy} & 0 \\ sh_{xz} & sh_{yz} & 1 & 0 \\ 0 & 0 & 0 & 1 \end{bmatrix}, I' = \begin{bmatrix} x' \\ y' \\ z' \\ 1 \end{bmatrix}$$

M being the geometric transformation matrix, I' the input image set, and I the final transformed image set.

The first affine transformation was a shear transformation and it was applied on the sagittal plane so that the tilted image volume could be resampled into the typical axial orientation. In order for that to happen all shear factors in the shear transformation matrix M were set to 0, except $sh_{zy}$. This factor determined the amount of shearing the image needed across the z axis and therefore was directly related to the CT gantry angle in which the image was acquired in.

Intuitively, the resampling of the titled slices required an interpolation due to the possibility of the voxels being moved off the grid points while untilting the image set, and for this project, we used a linear interpolation. The second affine transformation performed on the image was a scaling transformation. Similar to the matrix multiplication done for the shearing transformation, the scaling was performed by applying the appropriate factors on the M matrix, which were determined empirically to provide the best match between the reconstructed and the baseline image. Raw CT images acquired at an angle are elongated on the y-axis and therefore need a correction along that direction. For our setup, appropriate scaling was obtained when all elements of the identity matrix M were set to 0 except the position $M_{2,2}$, which scales the y-axis. This process was completed for the superior and inferior tilted images so that the new transformed image sets were then displayed as traditional axial slices and could be used in step 2.

Step 2: Correction of Metal Artifact

The superior and inferior modified image sets from step 1 were then used to reconstruct the final artifact reduced image. On each image set, this portion of the algorithm sifted axially through each pixel, starting at the superior-most slice, until it found the first metal thresholded pixel. The metal pixels are found by looking, slice by slice, for a pixel with a HU thresholded value that is equivalent to a metal value (e.g. a pixel value that represents a very high density material, including for example, metal). That slice number was saved and the same process was performed in opposite order starting from the inferior-most slice. That was done in order to determine the first and last slices on which artifacts were present. The number of slices with artifacts was dependent on the size of the implants and slice thickness, but in general, most images contained approximately 3.5 cm of artifact affected slices. Once those were identified, a center slice was calculated and used as the reference slice for that particular image set. The artifact free slices were selected in each image set, up to the reference slice. More specifically, the superior slices up to the reference slice in the superiorly tilted image set, and the inferior slices up to the reference slice in the inferiorly tilted image set. Finally, the artifact free slices were merged as shown in FIG. 2(c), and the final artifact reduced image was formed. In addition, the metadata in the final untilted image volume created required a correction. The post-reconstructed images were still assigned an angled metadata tag and had to be corrected in order to be properly displayed in the imaging software and in treatment planning systems.

WORKING EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 3:
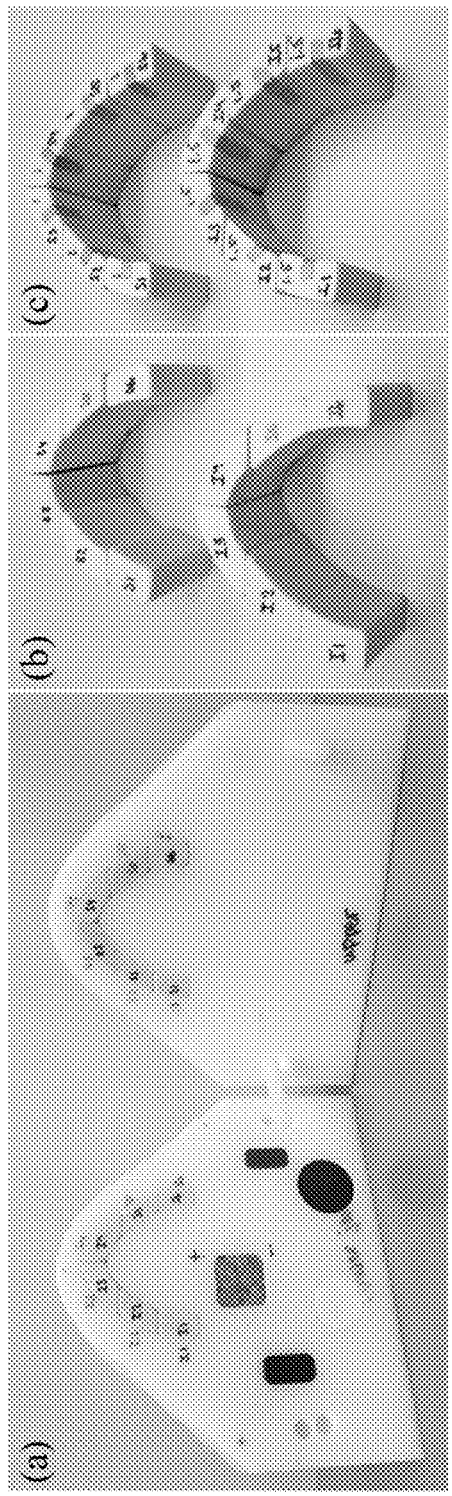
FIGS. 3A-C display both halves of a geometrical phantom, and the tooth structures used in the testing of the algorithm.

The routine described in the previous section was tested on a geometrical phantom simulating a head and neck cancer patient with dental fillings. The phantom was composed of high impact polystyrene and was divided into 2 halves, representing an upper and lower human jaw, so that tooth structures could be inserted (FIG. 3, panel (a)). The tooth structures were made of Gammex 450 cortical bone substitute (Middleton, WI). There were 2 sets of teeth used in the evaluation of the algorithm. The first one was used as the baseline and contained only the cortical bone material, in order to obtain the artifact free image set (FIG. 3 panel (b). The second set was modified to contain Dispersalloy® dental amalgam (Dentsply, Milford, DE) as seen in FIG. 3, panel (c). The general configuration and size of the dental fillings inserted in the modified set were determined by a dentist. The phantom was 15 cm×13.5 cm×8 cm and each tooth was approximately 3 cm long. The modified teeth set contains 1.5 cm long metal amalgam. FIG. 3 illustrates both halves of the geometrical phantom (shown in panel (a)) and the tooth structures (shown in panel (b)) used in the testing of the algorithm.

The geometrical phantom also contained plugs of different materials located posterior to the teeth set; these materials were selected to span the range of HU values seen in patients. There were 2 lateral rectangles made of solid water (1 cm×2 cm×2 cm) (CNMC Nashville, TN) and blue water (1 cm×2 cm×1 cm) (Gammex Middleton, WI), 2 cylinders made of PBT (dimeter: 2.5 cm×1 cm) and Techron HPV Bearing Grade (Gammex Middleton, WI) (dimeter: 2 cm×1 cm), and a cuboid made of cork (2 cm×2 cm×4 cm). These plugs were used as structures of interest in the phantom to help test the integrity of the algorithm and its ability to remove artifacts. Geometrical distortion and HU accuracy measurements were used to establish a comparison between the metal-free scan (baseline) and the reconstructed image set.

In order to quantify the potential distortion caused by the algorithm developed in this work, distance measurements of the different plugs and phantom were taken in the anterior-posterior (AP), left-right (LR) and superior-inferior (Z) directions. Measurements were done with the CT gantry at 0° with no metal teeth (baseline) and with metal amalgam (8 total metal teeth), at the 6 different gantry tilt angle reconstructions performed (5°, 10°, 15°, 20°, 25°, 30°). To maintain consistency throughout all the measurements, the plug dimensions were obtained by measuring the full width at half maximum (FWHM) on HU profiles across the center of each plug. HU accuracy testing was done measuring fixed ROI sizes throughout the different reconstructed scans. Mean HU numbers were collected inside each plug and compared between the baseline scan and reconstructed image set with reduced artifacts.

Techniques disclosed herein only require two scans, and the success of the artifact removal is not related to number of scans. In prior techniques, the multiples scans are combined based on variance maps. In embodiments of the present disclosure, the algorithm creates a final image based on the location and extent of the metal causing the artifacts.

Artifact Removal Attainment

Figure 4:
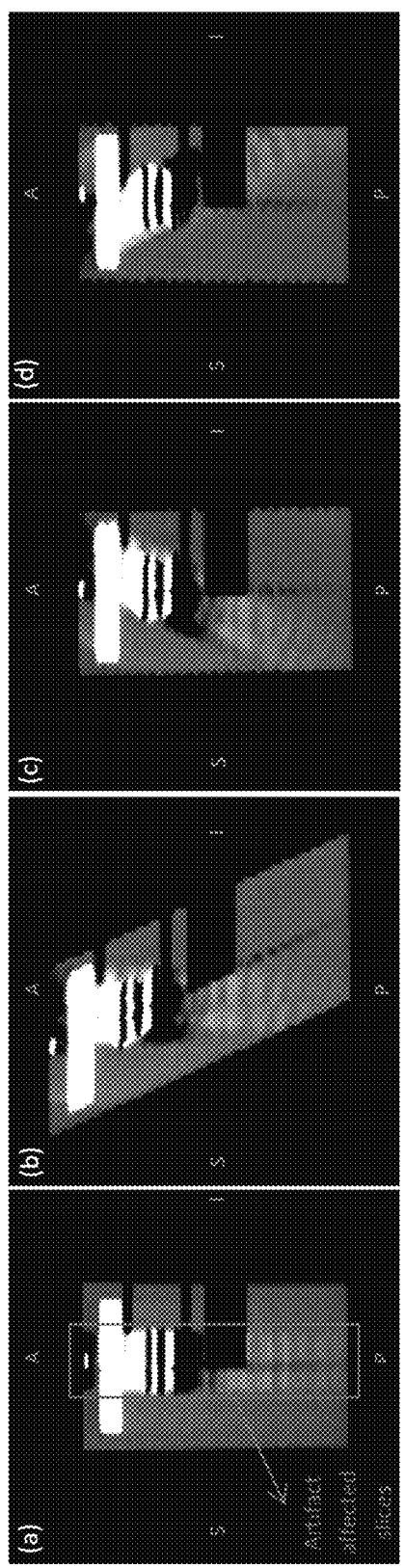
FIGS. 4A-D display a sagittal view of the raw image set of the geometrical phantom acquired at a 25° angle with metal teeth.

The first step of the algorithm developed in this work successfully untilted and corrected the angled CT image set. Referring now to FIG. 4, images are provided of a sagittal view of the raw image set of the geometrical phantom acquired at a 25° angle with metal teeth. The panels illustrate: (a) raw image acquired at an angle appearing tilted and elongated; (b) inferior tilted scan; (c) superior tilted scan; and (d) after the first part of the algorithm showing the desired typical axial appearance and corrected to normal height.

Panel (a) of FIG. 4 shows a sagittal screenshot of the 0° scan of the geometrical phantom with the metal teeth inserted and the artifacts created by them. As expected, the artifacts extended all the way through the posterior region of interest. Panel (b) of FIG. 4 demonstrates how the raw images acquired at an angle appear tilted and elongated. This particular example is a superior 25° tilt and shows the artifacts running perpendicular (AP) to the table. After the first part of the script was completed, the image set had the desired typical axial appearance (panel (c) of FIG. 4) showing the 2 halves of the phantom and its structures, as you would see in the regular perpendicular scan (panel (a) of FIG. 4), except with the artifacts extending away from the HN posterior region of interest. Panel (d) of FIG. 4 shows the end result for the inferiorly titled image set. It is important to notice the geometric distortion along the AP direction in the raw image set panel (b). The raw images acquired at an angle become elongated (in the AP direction only) in comparison to the real phantom size. Panels (c) and (d) of FIG. 4 show the phantom after the script was applied, corrected to normal height and untilted. In addition, when examining the 6 different CT gantry angles used in this study, it was possible to observe that the geometric distortion was directly proportional to gantry angle and was highest at the maximum CT gantry tilt of 30°, when not corrected.

Figure 5:
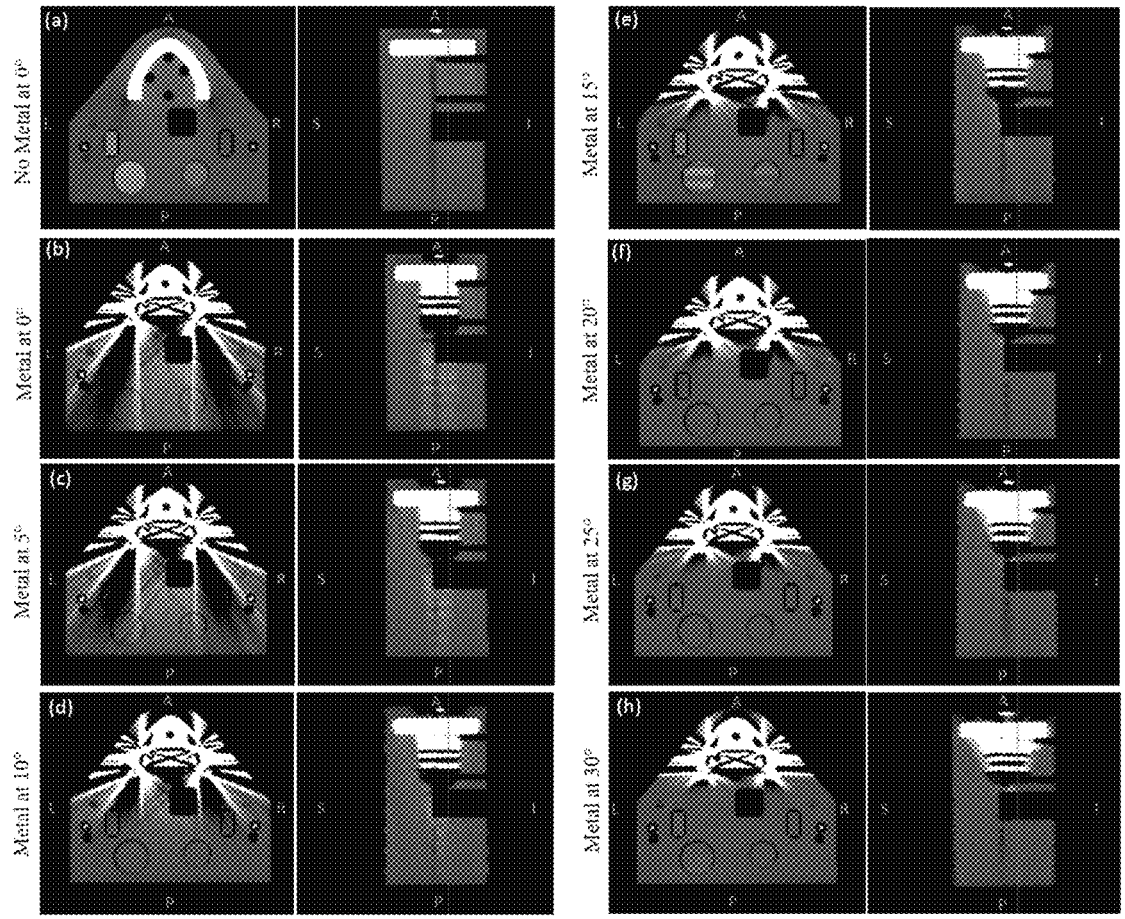
FIGS. 5A-H display axial and Sagittal views of geometrical phantom after the complete algorithm was applied.

The metal artifact reduction step of the algorithm design was successful at managing artifacts in the posterior region of the phantom. This can be seen in FIG. 5, which shows the axial and sagittal views of the geometrical phantom at the same slice location for each CT angle examined. The vertical yellow line on each sagittal view represents the corresponding axial image. It is possible to see that as the CT gantry angle increases, the posterior region of the metal artifacts created by the metal amalgam becomes clearer. As mentioned in the previous section, the artifacts in the reconstructed images remained in the mouth and chin regions, which can be seen more clearly on the larger angle reconstructions. However, those regions do not contain disease or OARs and are normally avoided in proton beam paths, thus not impacting the treatment planning process. FIG. 5 illustrates axial and sagittal views of a geometrical phantom after the complete algorithm was applied. The different panels illustrate: (a) no metal at 0°, (b) metal at 0°, (c) metal at 5°, (d) metal at 10°, (e) metal at 15°, (f) metal at 20°, (g) metal at 25°, (h) metal at 30°.

Algorithm Integrity Analysis

Figure 6:
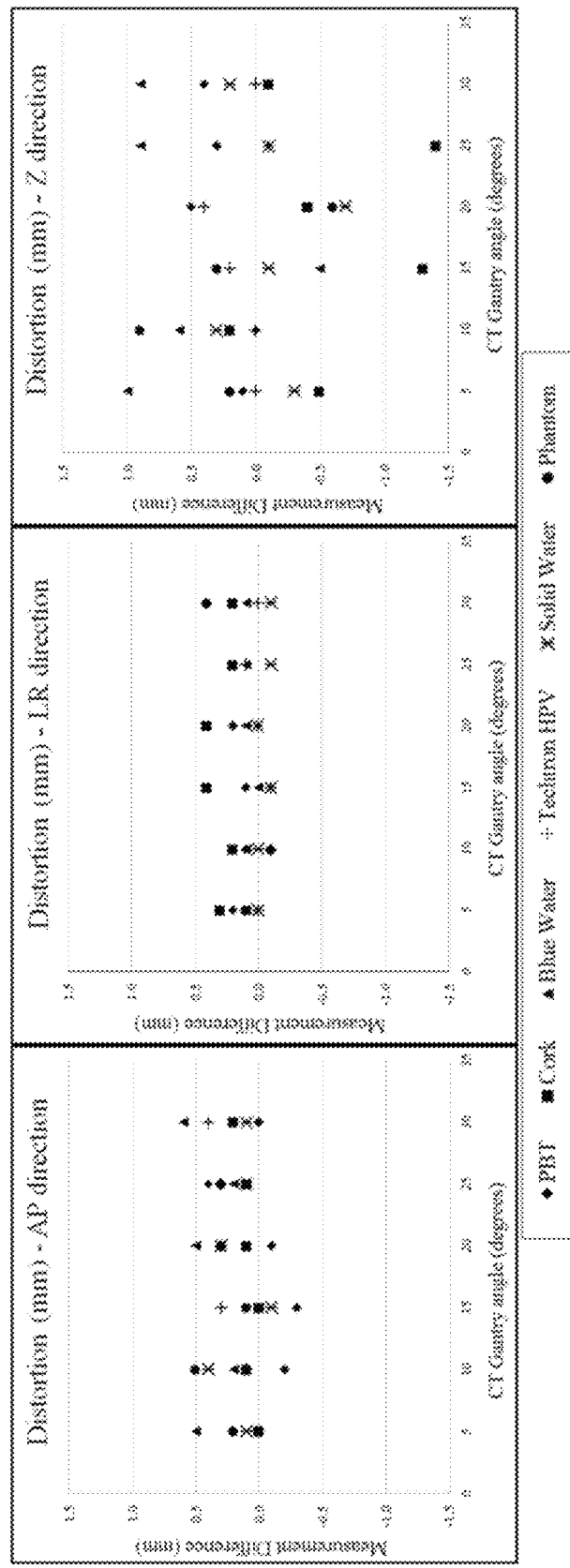
FIG. 6 displays results for distortion measurements obtained between the measurements of the different plugs and phantom done with the gantry at 0° with no metal teeth present and with metal teeth present for different CT gantry angles.

The results of the distortion measurements are shown in FIG. 6. Each data point represents the difference between the measurements of the plugs and phantom with the gantry at 0° with no metal teeth present (baseline) and with metal teeth present, for the 6 different CT gantry angles. It is possible to see that there is no trend in the measurements across the different gantry angles and different directions. Owing to the fact that no trend was observed, total averages were calculated for all the plugs and phantom measurements at each direction. The average total distortion for all gantry angles in the AP, LR and Z directions were 0.17 mm, 0.12 mm and −0.14 mm respectively. A negative value simply means that the measurement at an angle was smaller than the baseline measurement. In order to test the reproducibility of the measurement technique, the standard deviation (SD) was calculated for 2 sample materials; cork and Techtron HPV, representing the lowest and highest density materials. For each direction, 10 FWHM measurements were obtained and showed an average SD between the materials of 0.12 mm, 0.13 mm and 0.33 mm for the AP, LR and Z directions, respectively. FIG. 6 illustrates results for distortion measurements showing each difference obtained between the measurements of the different plugs and phantom done with the gantry at 0° with no metal teeth present (baseline) and with metal teeth present, for the 6 different CT gantry angles. In FIG. 6, results for distortion measurements show each difference obtained between the measurements of the different plugs and phantom done with the gantry at 0° with no metal teeth present (baseline) and with metal teeth present, for the 6 different CT gantry angles.

The measurement data for each material was fitted with a linear regression line and analyzed for statistical significance. An a level of 0.05 was used; all P-values calculated for the materials regression lines slopes' showed no significance, indicating there was no distortion pattern related to gantry angle. The fitted slopes varied from positive to negative with very small values, ranging from −0.05 to 0.014, again indicating no trend. In addition, all regression line intercepts' included 0 in the 95% Confident Intervals (CI), showing no evidence that the intercepts of the linear fit were positive or negative. The statistical analysis performed here showed that the measured geometrical distortion was random and not correlated with CT gantry angle.

Figure 7:
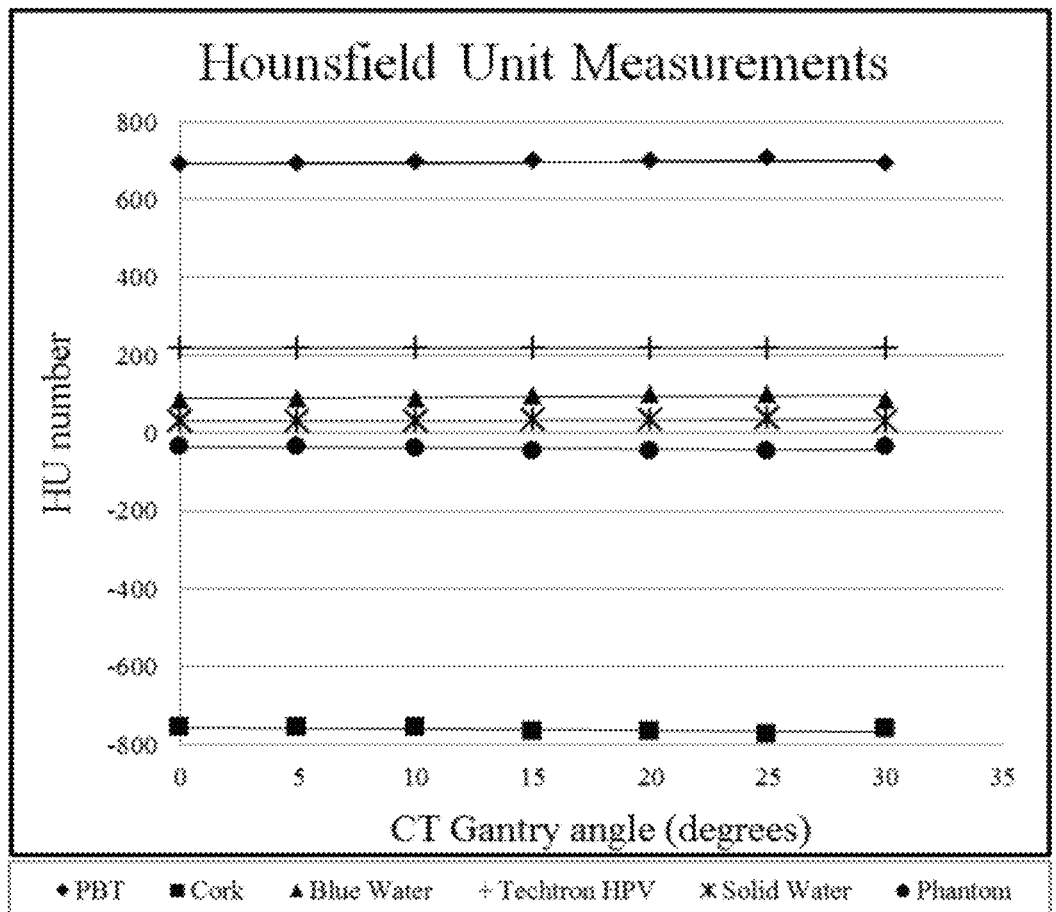
FIG. 7 is a graph displaying HU unit measurements of all materials obtained for the different CT gantry angles.

The HU measurements also showed no dependence with varying gantry angle and are shown in FIG. 7. Linear regression lines were also fitted for each material and the same regression analysis was performed as described above. Similar to the distortion measurements, all of the material slopes' P-values were above significance level, indicating no pattern correlating HU with gantry angle tilt. Additionally, for each material, the HU values measured were statistically consistent (within the 95% CI) with the true (untilted) HU value.

FIG. 7 illustrates HU unit measurements of all materials obtained for the different CT gantry angles.

Figure 8:
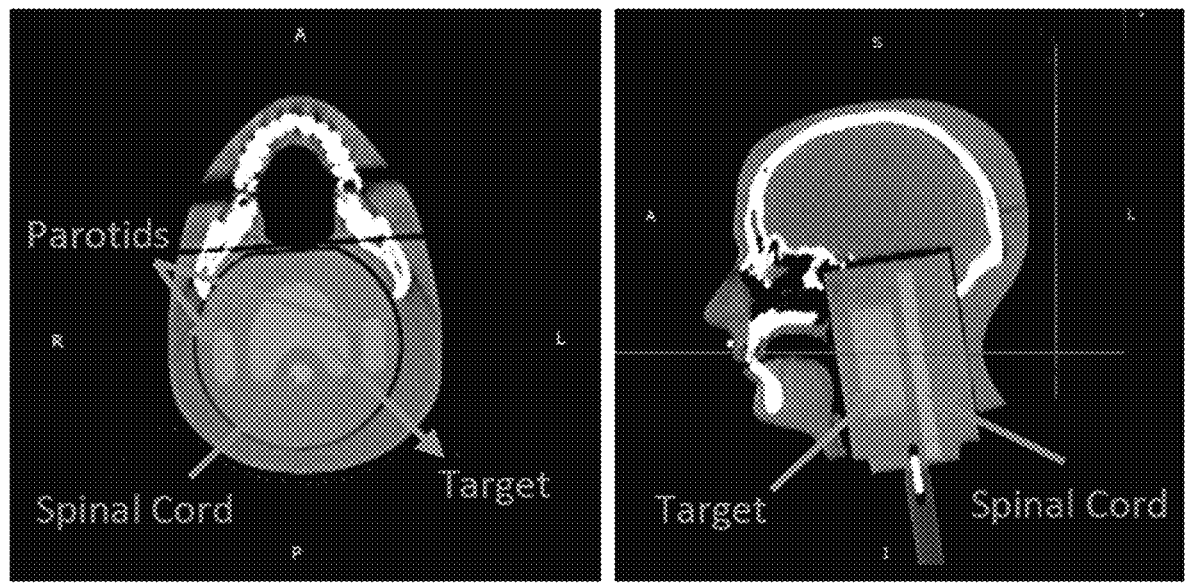
FIG. 8 is a scan displaying an Alderson phantom showing the insert that contains the target and structures at risk.

Referring now to FIG. 8, an image of an Alderson phantom is provided showing the insert that contains the target and structures at risk. The jaw cut allows for the teeth to be exposed and therefore be replaced with metal for the production of dental artifacts.

Figure 9:
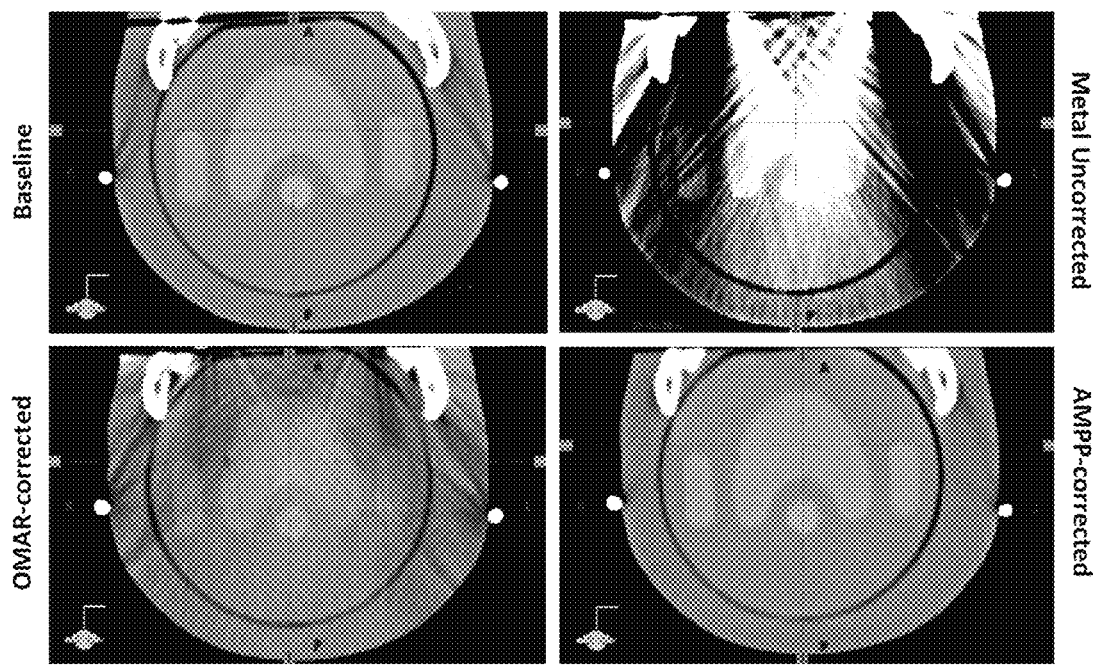
FIG. 9 displays a comparison of scans with different artifact reduction techniques.

FIG. 9 illustrates the baseline scan contains no dental artifacts and hence shows clearly the target and OARs located posteriorly to the oral cavity. The uncorrected scan shows the severity of the artifacts created and how it impacts the visualization of the structures contained in the phantom. OMAR shows some improvement, but creates additional artifacts in the image. The AMPP method provided significantly better visualization of targets and OARs, comparable to the baseline scan containing no metal.

Discussion

The algorithm generated in this work was successful at untilting and eliminating metal artifacts in the posterior region of the image. It is possible to see that as the CT gantry angle increases, the posterior region becomes clearer of metal affected pixels, leading to better visualization of the structures in the phantom. As a consequence of the combination of 2 angled scans, the artifacts extend to regions that were previously unaffected, such the nose and chin. However, as previously mentioned, those areas do not normally contain disease or OARs and are generally avoided as beam paths during treatment planning.

Several metal artifact reduction methods have been proposed and are currently available to the community. They range from the use of MVCT, dual energy CT and MRI, to the complete removal of the dental work. However, each has limitations and lacks wide clinical acceptance. A common technique in radiation oncology is to manually override HU values, but this has major drawbacks in that anatomy is still obscured and is now assumed to be homogeneous. Current metal artifact reduction algorithms are promising but have the downside of replacing missing data with artificially interpolated generated data. That approach creates additional uncertainty in the HU information, which is undesirable in diagnosis and in therapeutic dose calculations, particularly in applications such as proton therapy.

The metal artifact reduction technique presented in this work makes use of 2 angled CT scans with the goal of generating an accurate artifact free image. Unlike the existing algorithms, the one developed here uses the correct HU information to reconstruct the final image and does not rely on metal thresholded sinogram deletions and interpolation of data, which can cause more artifacts [13] and uncertainty in HU accuracy. The technique developed in this study also has the potential to be applied to other areas of the body that have metal inserts (surgical clips, prosthesis, etc) and therefore, has the potential for improvement in artifact management and imagining of anatomical structures previously not well defined.

The size difference measurements for all the plugs showed no statistically significant pattern when correlated with gantry angle, in all directions. Angled CT scans elongate the imaged object in the AP direction but these distortions were managed with the use of a geometrical correction applied in the first part of the algorithm. Following that correction, all distortion measurements were on the order of a tenth of a millimeter with similarly small standard deviations. Measuring the distances in the Z direction was more challenging due to worse resolution in that direction, yielding a larger observed standard deviation obtained in the Z direction, nearly 3 times that in the AP and LR directions. The poor Z direction resolution can be explained by the interpolation performed between the slices when the image set was being resampled into the typical axial orientation. Similar to the distortion findings, HU number was not correlated with gantry angle and showed high consistency throughout the different reconstructed images as compared to the baseline image set.

As mentioned before, the technique developed here manages metal artifacts with the use of correct/not-interpolated data but carries two intuitive limitations. The first is related to patient size and the potential for partial artifact removal. Larger patients may not permit the gantry to tilt to the larger angles available and therefore obtain less success from the algorithm. Nevertheless, as can be seen in FIG. 5, even a tilt of 10-15° can dramatically reduce artifacts. Another important drawback is the extra dose delivered to the patient by virtue of a second CT scan being used. However, the extra dose (~10 cGy) to the patient may be a reasonable compromise to improve the quality of diagnosis and/or radiotherapy treatment. Particularly in the setting of radiotherapy patients, this one-time extra dose is negligible when compared to the total treatment and imaging dose (<0.1%) already committed to HN patients.

The work performed in this manuscript was the first step in the algorithm routine analysis. The inventors intend to investigate the performance of the technique further in the context of radiation therapy. A dosimetric analysis will be performed on an anthropomorphic phantom investigating the success of the algorithm developed here compared to the other approaches currently being used. Proton treatment planning dose calculations and proton beam differences will be of particular interest due to their large dependency on HU accuracy and robustness.

ADDITIONAL EXAMPLES

Example 1—Image Quality Analysis of a Novel CT Metal Artifact Management Technique Against Four Major CT Vendor Techniques on an Anthropomorphic Head and Neck Phantom Background and Purpose: Perform a quantitative image quality analysis of our in-house-developed Artifact Management for Proton Planning (AMPP) algorithm for managing metal artifacts on head and neck (HN) CT scans by comparing it to major vendors' commercially approaches.

Materials and Methods: The metal artifact reduction (MAR) algorithms were evaluated using an anthropomorphic HN phantom with a removable jaw that allowed for the acquisition of images with and without (baseline) metal artifacts. The MARs algorithms from 4 major CT vendors were applied to the images with artifacts and the analysis was performed with each respective baseline. Percent of bad pixels from HU difference maps (between corrected and baseline images), along with HU volume differences were calculated.

Results: AMPP algorithm outperformed all of the vendors' commercially available approaches in the elimination of artifacts in the oropharyngeal region, showing the lowest percent of bad pixels, 4.2%; whereas those in the MAR-corrected images ranged from 25.5% to 65.5%. In terms of the entire volume of the affected slices, the current commercial MAR algorithms showed inconsistent performance, whereas the AMPP algorithm performed consistently well throughout the entire posterior region of the phantom.

Conclusions: A novel MAR algorithm was evaluated and compared to 4 currently available major commercial algorithms using an anthropomorphic HN phantom.

Unanimously, their performance was inferior to that of our in-house-developed AMPP algorithm. The AMPP algorithm has the potential to be broadly implemented, improve visualizations in patient anatomy and provide accurate, not interpolated HU information, helping with diagnosis as well as treatment planning in radiation oncology.

ABBREVIATIONS LIST

CT—Computed tomography
MAR—metal artifact reduction
OMAR—orthopedic metal artifact reduction
iMAR—iterative metal artifact reduction
SEMAR—single-energy metal artifact reduction
SmartMAR—Smart metal artifact reduction
AMPP—Artifact Management for Proton Planning
HU—Hounsfield Unit
OAR—Organs at Risk
kVp—Kilovoltage peak

1. Introduction

Head and neck scans represent almost 30% of all computed tomography (CT) scans done each year [1]. A substantial amount of these head and neck scans exhibit metal artifacts, particularly as produced by patients' dental work. These artifacts obscure tissues in the oral cavity and oropharyngeal region decreasing the ability to differentiate and delineate disease [2-4], potentially to leading to erroneous diagnoses. This problem is also relevant in radiation oncology where the CT scan is used for treatment planning; metal artifacts on CT images have been found to increase dose heterogeneity and reduce target coverage [3-5].

Several solutions for metal artifact reduction (MAR) have been proposed, but many are impractical, produce inaccurate CT images, and/or are not clinically available and therefore are not extensively adopted [5-10]. Major vendors also offer MAR algorithms for clinical use. While these algorithms contain proprietary information, they are known to be sinogram-based and work through the identification, deletion, and replacement of corrupted raw data. For example, Philips Healthcare offers an orthopedic MAR (OMAR) function, which is an iterative projection modification solution that performs several steps, including thresholding metal regions from the sinogram, removing them, and interpolating the missing data, to reconstruct the final artifact-adjusted image [11]. Similar to the OMAR function, Siemens Healthcare's iterative MAR (iMAR) algorithm removes high-contrast structures from the sinograms before interpolating the missing data [12]. GE Medical Systems' SmartMAR algorithm segments the metal data in the projection space and replaces those data with inpainted data [13]. Toshiba Medical's single-energy MAR (SEMAR) algorithm is also based on raw data segmentation and interpolation but incorporates different proprietary gradient correction features [14].

The effectiveness of existing MAR algorithms has been found to be partial. While these algorithms reduce the presence and severity of artifacts, this reduction is far from complete. Particularly for the difficult situation of the head and neck, typical algorithms were found to only reduce the severity and number by 15-30% [15]. Moreover, algorithms that manipulate the sinogram data estimate values to replace missing or suspected corrupted data instead of using true measured data. This process of estimating data can introduce inaccurate substitutions [9], possibly causing additional artifacts [16]. Hence, there is a clear need to improve metal artifact management, particularly in highly heterogeneous anatomical sites, such as the head and neck.

The purpose of this work was to perform a quantitative image quality analysis of our in-house-developed Artifact Management for Proton Planning (AMPP) algorithm for managing metal artifacts on head and neck CT scans by comparing the algorithm to major vendors' commercially available approaches. The technical details of the AMPP algorithm are presented in a separate paper, but the algorithm reconstructs the image using a pair of tilted scans. The reconstruction occurs in the image space and so are the post-processing steps, which can be applied on any scanner and do not require data interpolation or estimation only making use of unedited scan data. In this study we evaluated the quantity of image improvement and found that the AMPP algorithm outperformed all of the vendors' commercially available approaches in the elimination of artifacts in the oropharyngeal region.

2. Materials and Methods

2.1. Anthropomorphic Head and Neck Phantom

We designed an anthropomorphic head and neck phantom composed of tissue-equivalent materials [17], with a human skull and air cavities mimicking the tissue heterogeneities in patients. This phantom was based on an Alderson phantom (The Phantom Laboratory, Salem, NY) (FIG. 10a) modified to have a jaw insert and a cylindrical insert accessible from the bottom of the neck (FIG. 10b). The cylindrical insert, which was made of Solid Water (CNMC, Nashville, TN), enabled us to introduce soft-tissue features into the phantom, including a horseshoe-shaped "tumor" in the middle of the insert, 2 parotids lateral to the tumor, and spinal cord. These features were made of Blue Water (Gammex, Middleton, WI). The cylinder design was based on human anatomy representative of generalized oropharyngeal disease that is widely used for head and neck radiotherapy credentialing [18, 19].

The jaw insert enabled us to obtain images with and without metal artifacts. The lower jaw was cut to expose the top and bottom teeth. Holes were drilled in each of the 8 molars (4 superior and 4 inferior) to hold capsules made of either bone-equivalent material to simulate a case with no fillings (Techton HPV Bearing Grade; Gammex) or metal amalgams (Dispersalloy; Milford, DE) to simulate fillings and introduce metal artifacts. The locations, dimensions, and materials of the capsules were selected by a dental oncologist to be clinically realistic. The phantom with the metal amalgam capsules in place and the artifacts generated by them are shown in FIG. 10c.

2.2. Scans

The anthropomorphic phantom was scanned using Brilliance Big Bore (Philips Healthcare System), SOMATOM Definition Edge (Siemens Healthcare), Revolution HD (GE Medical Systems), and Aquilion PRIME (Toshiba Medical) CT scanners. Each scanner was used to acquire an image set with the bone-equivalent capsules (baseline scan) and an image set with the metal amalgam capsules (metal scan). Each metal scan was reconstructed using the respective vendor's MAR algorithm (corrected scan). The in-house AMPP algorithm was applied to image sets acquired with the Siemens SOMATOM Definition Edge scanner only, due to its performance being independent of CT scanner vendor (demonstrated in the robustness study of this manuscript). The parameters of each head and neck CT protocol used for the baseline and the metal scans are shown in Supplementary Materials.

2.3. Data Analysis

The MARs algorithms were evaluated using severity of artifacts criteria over a centrally located CT slice and HU number accuracy over the introduced structures in the phantom.

Planar Artifact Severity. We quantified artifact severity that remained after application of different MARs algorithms by comparing the HU maps of the MAR-corrected images with those of the corresponding baseline images for a central axial slice; for example, we compared OMAR-corrected scans with baseline scans obtained using the Philips scanner. To ensure that the same central slice of the phantom was compared across all platforms, the slices were selected with respect to fiducials positioned on the phantom. To ensure proper registration between the each baseline slice and its corresponding MAR corrected slice, we used rigid, intensity-based image registration in MATLAB. After image registration, we created HU error maps by subtracting each MAR-corrected image from its corresponding baseline image.

We calculated the percentage of bad pixels inside the circle that defined the phantom cylinder, which was considered the region of interest in the phantom that the algorithm aimed to improve. All pixels with a HU error above +20 HU or below −20 HU were considered to be bad pixels. The 20-HU threshold was based on the HU standard deviation obtained in the baseline scan. The average standard deviation calculated inside the baseline structure volumes was 8 HU; therefore, HU differences more than 2 standard deviations from the mean were considered to be too far from the baseline value and thus represented demonstrably erroneous pixels.

Structure HU number accuracy. The target and OARs on the baseline image were contoured using the Eclipse treatment planning system (version 13.6; Varian Medical Systems, Inc., Palo Alto, CA). Contours were extended superiorly-inferiorly through the artifact-affected slices (~1.5 cm). Thus, the HU number accuracy was quantified for the volumes of interest affected by artifacts (i.e., those posterior to the metal in the oral cavity). The volumes created on the baseline scans were copied onto the corrected metal scans to maintain consistency throughout the volumes analyzed. The mean HU numbers and standard deviations were measured inside each structure, and mean HU differences were calculated using each metal scan HU ($\overline{HU}_{MAR\ technique}$) and corresponding baseline scan HU ($\overline{HU}_{baseline}$) according to the following equation:

$$\overline{\Delta HU} = \overline{HU}_{MAR\ technique} - \overline{HU}_{baseline}$$

2.4. Robustness Evaluation

We evaluated the robustness of the AMPP algorithm by applying the algorithm to images acquired using several different scanning parameters. The imaging parameters are shown in Supplementary Materials. For example, to determine the extent to which CT x-ray tube energy affected the performance of the algorithm, we applied AMPP to images acquired at 100, 120, and 140 kVp. The AMPP-corrected scan was repeated at 120 kVp on a GE scanner to investigate the algorithm's independence of scanner type. The AMPP algorithm was also evaluated in the context of different slice thicknesses, filter types, head tilt statuses, and scanner-specific reconstruction algorithms. To obtain each baseline scan, we repeated each metal scan without the metal amalgam in place so that each AMPP-corrected scan was compared with a corresponding baseline scan obtained using the exact same imaging parameters. In each scenario, artifact severity was evaluated by assessing the percentage of bad pixels and HU number accuracy within the structures' volumes.

3. Results

3.1. Planar Artifact Severity

The effectiveness of the existing MAR algorithms is shown qualitatively in FIG. 11a-d; the AMPP-corrected image is shown in FIG. 11e. The same axial slice was chosen from each data set for the analysis. Each MAR algorithm diminished the severity of the artifacts in the uncorrected images (FIG. 10c) but with varying, and sometimes limited, success. In some instances, the MAR algorithms introduced additional artifacts in the posterior region characterized by a subtle ripple effect on the streaks (FIG. 11c). In contrast, the AMPP algorithm eliminated artifacts posterior to the oral cavity; the AMPP-corrected image was nearly identical to the corresponding baseline image (FIG. 10b). Immediately near the metal, none of the algorithms evaluated were able to reduce the artifacts due to the proximity to the metal implants. Hence only the posterior region of the phantom was evaluated in the analysis. This compromise was considered to be acceptable because that is mostly the area of interest in oropharyngeal disease.

The HU error maps show the quantitative differences between the corrected images and the corresponding baseline images in FIG. 12. There were severe differences, displayed by the dark red and dark blue colors, between the uncorrected image and corresponding baseline images. Compared with the uncorrected image, the MAR-corrected images were improved, but they still showed remarkable inconsistencies with the corresponding baseline images. In contrast, the AMPP-corrected image showed great agreement (within ±20 HU) with the baseline image, displaying a mostly green difference map inside and outside the phantom. The percentages of bad pixels in the circular region of interest that defined the cylinder in the phantom were 78.1%, 65.5%, 29.1%, 25.5%, 27.9% and 4.2% for the uncorrected, OMAR, SEMAR, iMAR, SmartMAR and AMPP techniques respectively.

3.2. Structure HU Number Accuracy

For a volumetric analysis of the affected slices, the mean HU errors in the structure volumes in the phantom for the uncorrected and corrected images are shown in Table 1. The columns show the mean HU differences for each metal scan corrected by a MAR algorithm and its respective baseline. A difference close to 0 means that the algorithm improved the HU numbers within all volumes compared to the uncorrected scan. A negative number means the baseline HU value in that structure was larger than on the metal corrected scan. The commercial MAR algorithms provided different degrees of improvement depending on structures; notably, there were structures that had systematic average HU errors in excess of 20 HU, and all vendor algorithms had structures with average systematic errors of at least 15 HU. The AMPP algorithm consistently outperformed the commercial algorithms, regardless of location or anatomy, and improved the HU accuracy to nearly the same as that of the uncorrected baseline scan; the maximum systematic HU error was only 2 HU. The standard deviations in each structure volume for the baseline, uncorrected, and corrected images are shown in Table 2. As expected, the uncorrected image had the largest standard deviation owing to the many high- and low-density streaks within the phantom. The MAR algorithms showed some improvement but did not perform as well as the AMPP algorithm, which yielded standard deviations similar to the baseline values.

TABLE 1

Mean HU errors within each structure volume inside the phantom by correction technique.

| Structure | Mean HU error within Structure Volume (HU) | | | | | |
|---|---|---|---|---|---|---|
| | Uncorrected | OMAR | SmartMAR | iMAR | SEMAR | AMPP |
| PTV | 39 | −18 | 2 | −15 | −3 | −2 |
| Spinal Cord | 36 | −13 | 3 | −13 | −1 | −1 |
| Right Parotid | −67 | −34 | −15 | 3 | −20 | 2 |
| Left Parotid | −63 | −36 | −24 | −4 | −19 | 1 |

TABLE 2

HU standard deviation (SD) of each structure volume inside the phantom by correction technique.

| Structure | HU SD within Structure Volume (HU) | | | | | | |
|---|---|---|---|---|---|---|---|
| | Baseline | Uncorrected | OMAR | SmartMAR | iMAR | SEMAR | AMPP |
| PTV | 8 | 41 | 25 | 13 | 27 | 13 | 6 |
| Spinal Cord | 9 | 21 | 19 | 10 | 21 | 13 | 9 |
| Right Parotid | 11 | 49 | 19 | 9 | 16 | 17 | 7 |
| Left Parotid | 6 | 43 | 23 | 13 | 15 | 13 | 6 |

3.3. AMPP Robustness Evaluation

The percentages of bad pixels and mean HU errors for the different imaging parameters under which the AMPP-corrected images were acquired are shown in Table 3. The AMPP algorithm performed similarly regardless of imaging parameter; each AMPP-corrected image showed similarly small HU differences and a small percentage of bad pixels as compared with the corresponding baseline images.

TABLE 3

Mean HU errors within structure volumes and percentages of bad pixels for different imaging parameters under which the AMPP-corrected images were acquired

| | Mean HU error (HU) | | | | | | | |
|---|---|---|---|---|---|---|---|---|
| Structure | Energy, 100 kVp (Siemens) | Energy, 120 kVp (GE) | Energy, 120 kVp (Siemens) | Energy, 140 kVp (Siemens) | Slice Thickness | SFOV | Head Tilt | Recon Algorithm |
| PTV | −1 | 4 | −2 | −1 | 0 | 0 | −2 | 0 |
| Spinal Cord | 0 | −2 | −1 | 0 | 0 | 0 | −2 | 2 |
| Right Parotid | 2 | −3 | 2 | 1 | 4 | −1 | −3 | 2 |
| Left Parotid | 2 | 6 | 1 | −1 | 3 | 6 | −2 | 2 |
| % Bad Pixels | 1.5 | 1.4 | 4.2 | 0.8 | 3.8 | 2.5 | 2 | 2.6 |

4. Discussion

On the basis of HU number information, all MAR algorithms reduced the percentage of bad pixels, at varying degrees of efficacy. Although the OMAR-corrected images retained several artifacts and thus still had a large percentage of bad pixels, the SEMAR, iMAR, and SmartMAR algorithms reduced the percentage of bad pixels by factors of 2-3. In contrast, the AMPP algorithm reduced the percentage by a factor of 20. In terms of the entire volume of the affected slices, the current commercial MAR algorithms showed inconsistent performance; whereas the SmartMAR and SEMAR algorithms performed well where the target and spinal cord were defined, the iMAR algorithm performed well where the parotids were defined. In contrast, the AMPP algorithm performed consistently well throughout the entire posterior region of the phantom, regardless of the location and intensity of the metal artifacts. This was true both in terms of eliminating systematic HU errors as well as minimizing any spread in the HU over the structure. Our findings also show that the AMPP algorithm performed well under different CT image acquisition parameters. The percent of bad pixels achieved with the AMPP algorithm under different parameters were all similar to each other and smaller than those achieved with the commercial MAR algorithms, ranging from 0.8% to 4.2%, whereas those in the MAR-corrected images ranged from 25.5% to 65.5%. That the AMPP algorithm is robust, as well as independent of scanner type and imaging parameters, is important for its clinical application. These results suggest that the AMPP algorithm, whose performance exceeded that of all currently available commercial algorithms in the current study, can be applied to any scanner that allows for gantry tilts.

The results of this study hinge on the accurate registration of the image sets as described in the methods section. Good registration was evaluated visually, but in addition, we also investigated the sensitivity of the results to the image registration process. To investigate the impact of an incorrect registration, we shifted the AMPP-corrected image 1 and 2 pixels compared with the baseline image and reassessed the percentage of bad pixels in the corrected image. Whereas the bad pixel percentage of the original AMPP-corrected image was 4.2%, that of the AMPP-corrected image with a misalignment of 1 pixel was 5.9%, and that of the AMPP-corrected image with a misalignment of 2 pixels was 11.8%. The figure showing the error maps for the incorrect registrations is shown in Supplementary Materials. It is possible to see the outline of the target and OARs as the pixel offset increases. However, the percentage of bad pixels on the obviously poorly registered AMPP-corrected images were still much lower than those on the MAR-corrected images, suggesting that the registration process was robust.

In this study, a novel MAR algorithm was evaluated and compared to 4 currently available major commercial algorithms; OMAR (Philips Healthcare System), SmartMAR (GE Medical Systems), iMAR (Siemens Healthcare) and SEMAR (Toshiba Medical). An anthropomorphic head and neck phantom was designed and used to perform the analysis by providing a method for obtaining metal free scans (baseline) and artifact filled scans (with metal amalgam). Although commercial MAR algorithms generally reduced the severity of metal artifacts in head and neck CT scans, the algorithms performed slightly differently from each other, consistent with their individual proprietary distinctions. Unanimously, their performance was inferior to that of our in-house-developed AMPP algorithm. The AMPP algorithm has the potential to be broadly implemented, improve visualizations in patient anatomy and provide accurate, not interpolated HU information. This can help with diagnosis as well as treatment planning in radiation oncology. In future studies, we will evaluate the proton therapy dosimetric performance of the MAR algorithms investigated in the present study.

Example 2—Dosimetric Impact of Commercial CT Metal Artifact Reduction Algorithms and a Novel In-House Algorithm for Proton Therapy of Head and Neck Cancer Purpose: We compared the dosimetric impact of all major commercial vendors' metal artifact reduction (MAR) algorithms to one another, as well as to a novel in-house technique (AMPP) using an anthropomorphic head phantom.

Materials and Methods: The phantom was an Alderson phantom, modified to allow for both artifact-filled and baseline (no artifacts) CT scans using teeth capsules made with metal amalgams or bone-equivalent materials. It also included a cylindrical insert that was accessible from the bottom of the neck and designed to introduce soft tissue features into the phantom that were used in the analysis. The phantom was scanned with the metal teeth in place using each respective vendor's MAR algorithm: OMAR from Philips, iMAR from Siemens, SEMAR from Canon, and SmartMAR from GE; the AMPP algorithm was designed in house. Uncorrected and baseline (bone-equivalent teeth) image sets were also acquired using a Siemens scanner. Proton spot scanning treatment plans were designed on the baseline image set for five targets in the phantom. Once optimized, the proton beams were copied onto the different artifact-corrected image sets, with no reoptimization of the beams' parameters, to evaluate dose distribution differences in the different MAR-corrected and -uncorrected image sets. Dose distribution differences were evaluated by comparing dose volume histogram (DVH) metrics, including planning target volume D95 and clinical target volume D99 coverages, V100, D0.03 cc, and heterogeneity indexes.

Results: Uncorrected CT metal artifacts and commercial MAR algorithms negatively impacted the proton dose distributions of all five target shapes and locations. No commercial algorithms affected the dose distributions in a consistent manner, either by overdosing or underdosing the planning target volumes. The AMPP-corrected images, however, provided dose distributions that consistently agreed with the baseline dose distribution. The results of these dosimetry evaluations suggest that the commercial MAR algorithms' performances varied more with target location and less with target shape. The targets were located close to the oral cavity and were therefore subject to more severe artifacts; their dose distributions showed greater variation, likely due to the inadequate HU correction from commercial MAR algorithms, which was sometimes worse than no correction at all.

Conclusions: CT metal artifacts negatively impacted proton dose distributions on all five targets analyzed. The commercial MAR solutions performed inconsistently throughout all targets compared to the metal-free baseline. A lack of CTV coverage and an increased number of hotspots were observed throughout all commercial solutions. Dose distribution errors were related to the proximity to the artifacts, demonstrating the inability of commercial techniques to adequately correct severe artifacts. In contrast, AMPP consistently showed dose distributions that best matched the baseline, likely because it makes use of accurate HU information, as opposed to interpolated data like commercial algorithms.

1. INTRODUCTION

Metal dental fillings are common and can create severe imaging artifacts on computed tomography (CT) imaging in head and neck (HN) cancer patients. These artifacts can seriously affect disease diagnosis, as well as subsequent radiation treatment planning.[1-3]

Dental CT artifacts are characterized by dark and bright streaks throughout the image slices, resulting in incorrect Hounsfield unit (HU) number designations and blurring of anatomy. High-atomic number metals strongly attenuate the CT signal, leading to an incorrect HU calculation and assignment during the image reconstruction process. This selective attenuation phenomenon is called beam hardening and is the fundamental cause of CT metal artifacts.[4] Image reconstruction algorithms attempt to correct for this polyenergetic nature of the x-ray spectrum but are not optimized for highly attenuating materials such as metal. In addition to beam-hardening effects, high-density materials create increased scatter and photon starvation in the detectors that adds to the deterioration of the resulting CT images. Techniques that reduce noise by increasing tube potential and mAs, as well as the use of adaptive filtering, only partially alleviate image quality issues.[5]

One currently available strategy for addressing metal artifacts in CT images is the use of commercial artifact reduction algorithms. In general, metal artifact reduction (MAR) algorithms work through the detection and removal of corrupted data, followed by the interpolation of the data and reconstruction of the final CT images. Each commercial vendor offers a unique algorithm that differs in its approach to estimating the missing data; these approaches include linear interpolation, sinogram normalization, and tissue class modeling,[6-8] all of which can result in substantial differences in the final reconstructed images.[9]

Reducing artifacts using MAR algorithms is less subjective and time consuming than are the typical manual HU-overriding techniques that are used in the clinic. However, in CT images with metal artifacts, sinogram manipulation needs to be considered carefully, as its success is highly dependent on the accurate estimation of the new interpolated values. Sharp transitions between original projections and estimated projections can create additional unwanted artifacts,[10] and data loss near the metals can cause blurring in the image.[11] Moreover, commercial MAR algorithms have been found to be substantially ineffective at resolving artifacts.

In addition to the potential for data loss and introduced artifacts, commercial algorithms are not always successful at reducing artifact severity. Most studies of these algorithms have only been performed in simple environments, such as homogenous geometrical phantoms with qualitative endpoints.[12-14] Huang et al. investigated three currently available commercial MAR algorithms on a heterogeneous anthropomorphic phantom and concluded that they were not successful at reducing artifacts caused by dental fillings; they also introduced new artifacts in adjacent image planes.[15]

The success of commercial MAR algorithms in dose calculation[16, 17] has been substantially limited to photon therapy; the impact of these algorithms on proton radiation therapy is unknown. A key component of accurate proton therapy planning is knowing the exact range of the protons as they travel through the patient. The precise location of the distal dose gradient in patients needs to be predicted accurately to fully take advantage of protons' sharp fall-off at the distal end of the dose distribution; any uncertainty in the range will result in uncertainty in the location of the dose deposition. One important source of uncertainty is incorrect HU assignment in CT images.[18] The accuracy of proton dose calculations is directly related to the conversion schemes implemented to relate HU information to relative stopping power. The purpose of this study was to compare the dosimetric impact of all major vendors' MAR algorithms and a novel stereoscopic technique that was developed in house, AMPP,[19] in an anthropomorphic HN phantom. AMPP uses CT gantry tilts instead of sinogram manipulation or direct interpolation methods as in commercial options.

2. MATERIALS AND METHODS

2.A. Anthropomorphic Phantom

A realistic anthropomorphic HN Alderson phantom (The Phantom Laboratory, Salem, NY) that was composed of tissue-equivalent materials[20] with a human skull and air cavities that mimicked the tissue heterogeneities found in patients. The phantom was modified to allow for both artifact-filled and baseline (no artifacts) CT scans. The lower jaw was cut to expose the top and bottom teeth, and holes were drilled in each of the eight molars (four superior and four inferior). We created capsules using bone-equivalent material in proton beams;[21] these were inserted into molars to simulate no fillings (Techton HPV Bearing Grade; Gammex). We used capsules made with metal amalgams (Dispersalloy; Milford, DE) to simulate fillings and introduce metal artifacts. The locations, dimensions, and materials of the capsules were selected by a certified dentist to be clinically realistic.

In addition to the jaw modification, we designed a cylindrical insert that was accessible from the bottom of the neck; the insert introduced soft tissue features into the phantom, including a horseshoe-shaped target in the middle of the insert and two lateral parotids and a spinal cord posterior to the target that served as organs at risk (OARs). The design describes a generalized oropharyngeal disease and shares dimensions with the IROC proton HN phantom used for clinical trial credentialing.[22] The cylindrical insert and structures were made of Solid Water (CNMC, Nashville, TN) and Blue Water (Gammex, Middleton, WI), respectively. FIG. 13(a) shows the axial and sagittal CT scans of the phantom, including the structures described above in the cylindrical insert without the dental amalgams in place. FIG. 13(b) shows a CT scan of the HN phantom in which the bone-equivalent teeth structures were replaced by the metal amalgams, creating streaking artifacts that can be visualized in the axial and sagittal views.

2.B. CT Image Sets and MAR Algorithms

The anthropomorphic phantom was scanned using the Brilliance Big Bore (Philips Healthcare System, Bothell, WA), SOMATOM Definition Edge (Siemens Healthcare, Forchheim, Germany), Revolution HD (GE Medical Systems, Waukesha, WI), and Aquilion PRIME (Canon Medical Systems USA, Tustin, CA) CT scanners. To maintain positional consistency throughout all scans, the phantom was aligned in the supine position using a Klarity mold and fiducials. Each scanner was used to acquire an image set with the metal amalgam capsules in place to generate the artifacts. Each metal scan was reconstructed using the respective vendor's MAR algorithm: OMAR from Philips, iMAR from Siemens, SmartMAR from GE, SEMAR from Canon, and AMPP as our in-house algorithm. The AMPP algorithm was applied to an image set acquired with the Siemens scanner without the vendor's MAR algorithm in place. We also acquired an uncorrected image (based on the Siemens scan) and a baseline scan in which the bone-equivalent capsules were used, resulting in an artifact-free image. The imaging parameters (kVp, slice thickness, mA, scan field of view, head tilt, and reconstruction type) of each scan are shown in Table 4. CT scan parameters were kept as similar as possible.

2.C. Treatment Planning

The proton spot scanning treatment plans were designed using the Eclipse treatment planning system (version 13.6; Varian Medical Systems, Inc., Palo Alto, CA) on the baseline image set, following the treatment planning guidelines used by the MD Anderson Proton Therapy Center (Houston, TX). Two anterior oblique beams and a posterior beam were used to deliver a prescription of 60 Gy to the horseshoe target shown in FIG. 14(a). Despite not being visibly present in the CT images, additional target shapes and sizes (FIG. 14(b-e)) were contoured within the insert to further determine the performance of the MAR algorithms at different anatomical locations. The additional four target contours, designated bean, sphere, dot, and X, were based on actual human disease locations and shapes treated at the MD Anderson Proton Therapy Center and are shown in FIG. 14(f-j). The treatment planning parameters used for each target's plan were based on clinical arrangements and can be found in Table 2 below.

TABLE 5

Treatment planning parameters used for each target's proton plan designed on the baseline.

| Target and planning parameters | Field 1 | Field 2 | Field 3 |
|---|---|---|---|
| Horseshoe | | | |
| Angle | 180 | 65 | 295 |
| Couch rotation | 0 | 350 | 10 |
| Field weight | 1 | 1 | 1 |
| Collimator rotation | 0 | 0 | 0 |
| Bean | | | |
| Angle | 180 | 80 | 175 |
| Couch rotation | 0 | 0 | 0 |
| Field weight | 1 | 1 | 1 |
| Collimator rotation | 0 | 0 | 0 |
| Sphere | | | |
| Angle | 180 | 255 | 275 |
| Couch rotation | 0 | 0 | 0 |
| Field weight | 1 | 1 | 1 |
| Collimator rotation | 0 | 0 | 0 |
| Dot | | | |
| Angle | 180 | 80 | 275 |
| Couch rotation | 0 | 0 | 0 |
| Field weight | 1 | 1 | 1 |
| Collimator rotation | 0 | 0 | 0 |
| X | | | |
| Angle | 180 | 80 | 280 |
| Couch rotation | 0 | 0 | 0 |
| Field weight | 1 | 1 | 1 |
| Collimator rotation | 0 | 0 | 0 |

TABLE 4

Head and neck CT protocols used for the baseline and metal scans.

| MAR TECHNIQUE | CT VENDOR | ENERGY (KVP) | SLICE THICKNESS (MM) | MA | FOV | PHANTOM HEAD TILT | RECON TYPE |
|---|---|---|---|---|---|---|---|
| BASELINE | Siemens | 120 | 2 | 300 | Head | No | Standard |
| UNCORRECTED | Siemens | 120 | 2 | 300 | Head | No | Standard |
| OMAR | Philips | 120 | 3 | 300 | Head | No | Standard |
| SEMAR | Toshiba | 120 | 3 | 280 | Head | No | Standard. |
| IMAR | Siemens | 120 | 2 | 300 | Head | No | Standard |
| SMARTMAR | GE | 120 | 2.5 | 300 | Head | No | Standard |
| AMPP | Siemens | 120 | 2 | 300 | Head | No | Standard |

Each targets' plan was designed on the basis of the baseline image set with a beam arrangement, as depicted in Table 2. Multi-field optimization was used in all plans to achieve the best target coverage. Once optimized, the proton beams were copied onto the different artifact corrected image sets without reoptimization of the beams' parameters. This step was used to evaluate dose distribution differences once the beams were placed in the MAR-corrected and -uncorrected image sets. An additional step was used to address the positioning of the phantom on the different CT scanner couches. The dose grid used was considered to be inside of the body contour of the phantom to avoid dose calculation errors that originated from variations in CT table HU numbers. The body contour was copied onto all image sets so that the same dose grid was used.

2.D. Data Analysis

We evaluated the proton dose distributions' differences for the various targets and MAR algorithms by comparing typical clinical dose volume histogram (DVH) metrics, including planning target volume D95 (PTV D95) and clinical target volume D99 (CTV D99) coverages, V100, D0.03 cc, and heterogeneity indexes. Since these metrics are dependent on the volume of the structures being evaluated, each target was copied from the baseline onto the other image sets to maintain consistency between all volumes. The extent of all targets in the superior-inferior direction was 1.8 cm and was chosen to include the slices that contained artifacts. In addition to using the DVH metrics, we performed a qualitative assessment of the MAR-corrected dose distributions compared to the baseline dose distribution.

3. RESULTS

Figures 15A, 15B, 15C:
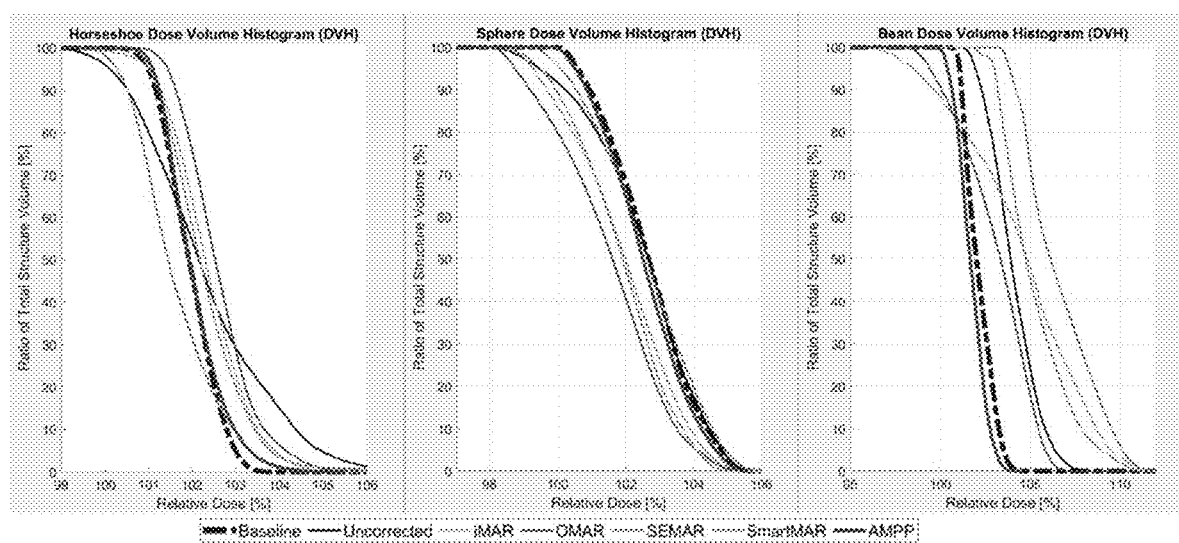
FIGS. 15A-C display DVHs for (a) horseshoe, (b) sphere, and (c) bean CTVs comparing all of the MAR-corrected and -uncorrected images.

Clinically realistic plans were designed and optimized for each of the PTVs on the baseline image set. The dose distributions from the baseline plans were copied onto the MAR-corrected and -uncorrected images; the DVHs differed substantially from the baseline DVHs. This was observed for all five target shape and location combinations. Representative DVHs for the horseshoe-, bean-, and sphere-shaped targets are shown in FIG. 15.

In general, the target DVHs from the commercial MAR algorithms showed both underdosing or overdosing of the target, depending on the algorithm used to correct the artifacts and the anatomical location of the target. For example, for the bean target, most algorithms systematically overestimated the dose to the target by as much as 5%-6%. For the sphere target, most algorithms systematically underestimated the dose by 1%-2%. However, the patterns were varied. Also of note is the black line in the figure, which shows the result when no metal artifact reduction strategy was applied. This result was comparable, and often superior to, those of the commercial MAR solutions from the vendors, indicating that the vendor solutions were not particularly successful at mitigating the impact of the artifacts. However, the in-house algorithm, AMPP, showed DVHs that were highly similar to those of the baseline (no metal amalgams) proton plan (FIG. 15), indicating that AMPP was the best image set for performing the proton dose calculations for all targets.

The baseline treatment plans generated on metal-free baseline images served as a reference for the MAR technique comparisons. All plans had PTV D95 and CTV D99 target coverages that were clinically acceptable, per review by an MD Anderson radiation oncologist, and CTV V100 and D0.03 cc values that were within the clinical recommendations. In contrast, the DVH metrics that were extracted from the plans and copied onto the artifact-corrected and -uncorrected images varied greatly depending on the algorithm used to correct the artifacts and the location of the target. Table 3 shows a comprehensive view of the DVH metrics for each target shape and image set, with each value ordered from lowest to highest. Since the DVH metrics are a representation of the DVH curves, these data are consistent with those shown in FIG. 15 and indicate that no commercial MAR algorithm consistently reproduces the same result as the baseline; the data are also inconsistent in how the deviations manifest on the basis of the target shape and location. AMPP, however, showed consistently similar DVH metrics for all targets compared to the baseline and for all of the metrics evaluated.

FIG. 19 shows planning evaluation metrics for all targets included in this study. The baseline and AMPP plans are highlighted for ease of comparison. Underlined numbers show the correlation between V100 and D0.03 cc values, indicating an overdose (larger D0.03 cc) rather than quality target coverage (V100=100).

Figure 16A:
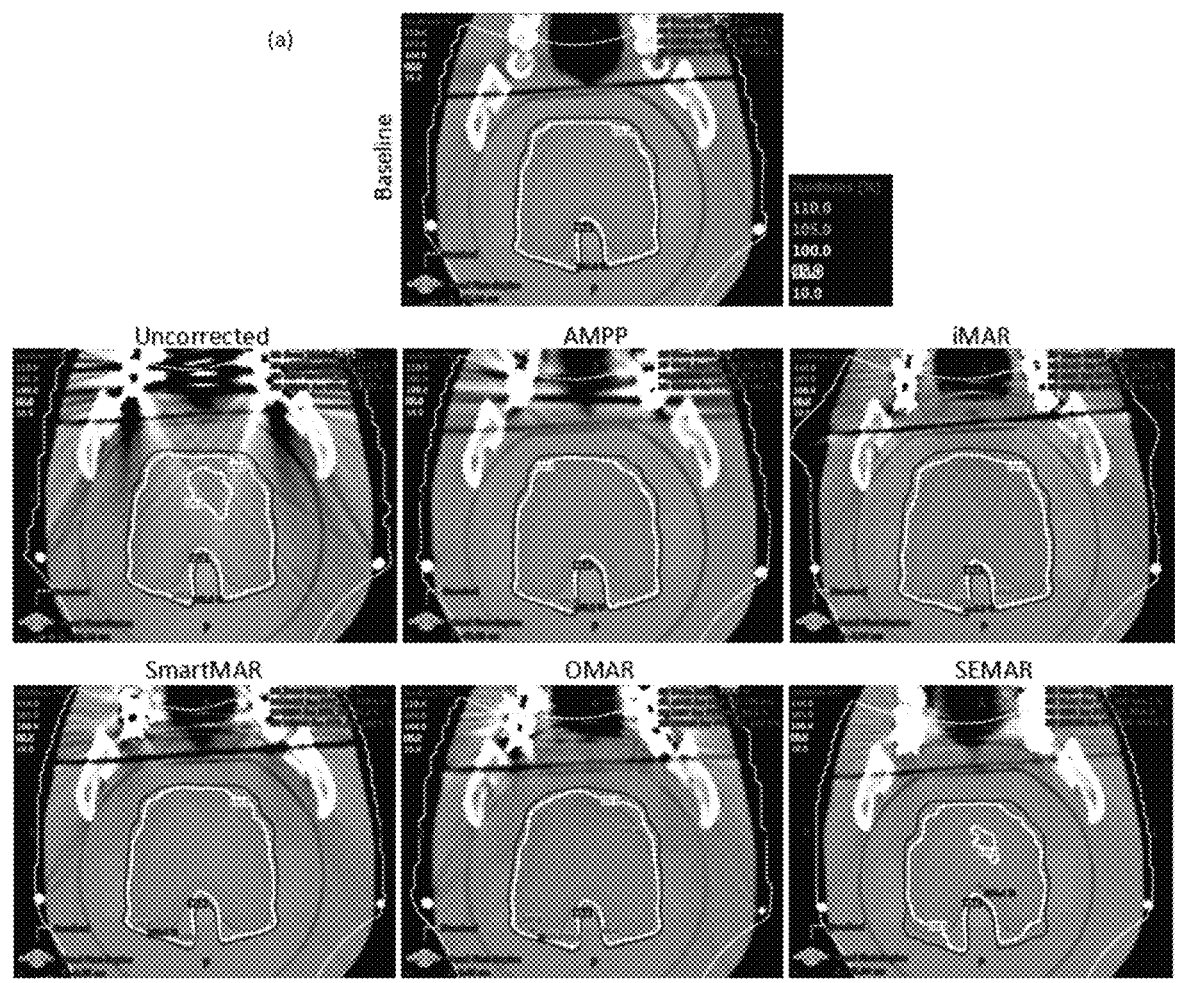
FIGS. 16A-C display an axial view of the anthropomorphic phantom showing the proton dose distributions for (a) horseshoe, (b) sphere, and (c) bean targets. Each PTV is shown in red for all of the different MAR-corrected and -uncorrected image set.
Figure 16B:
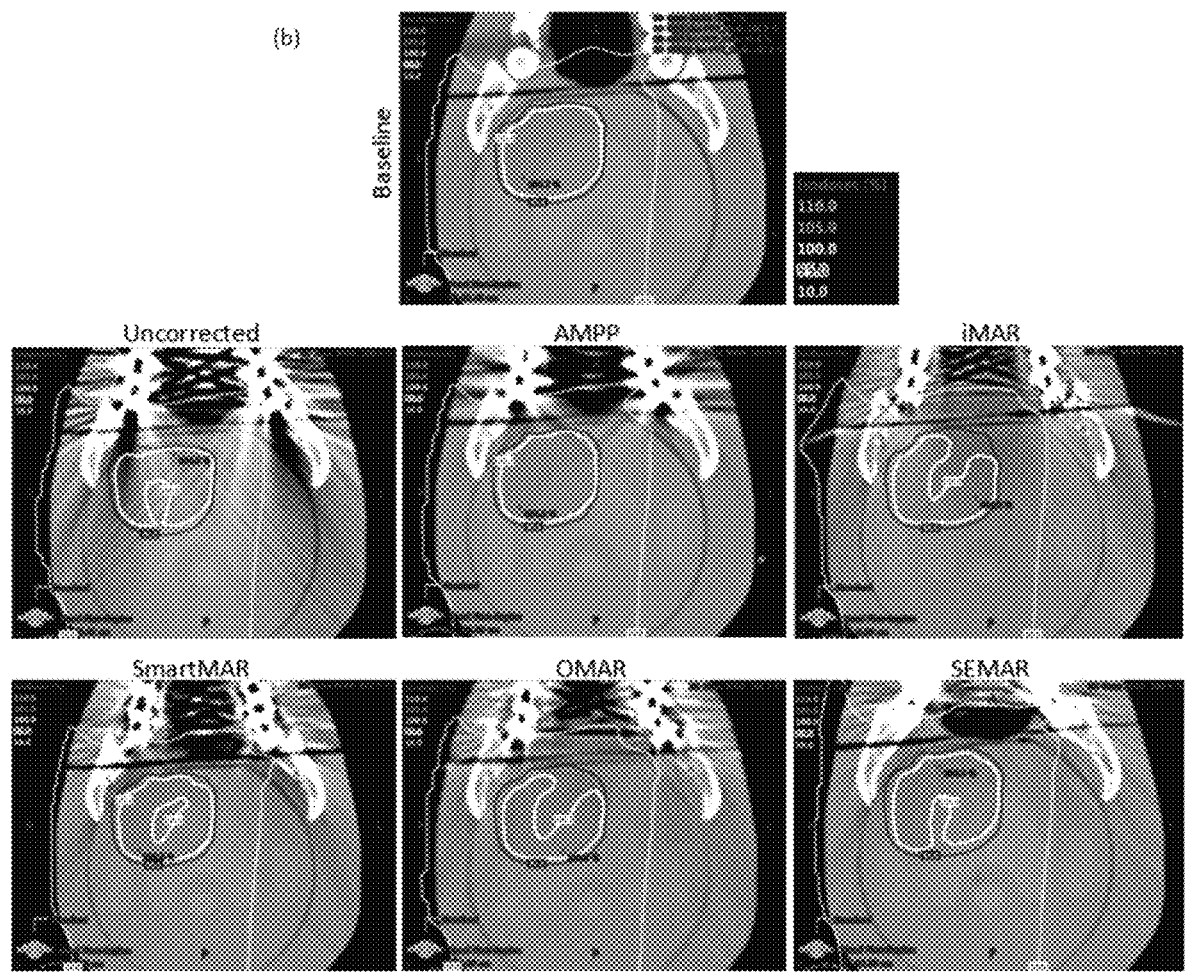
Figure 16C:
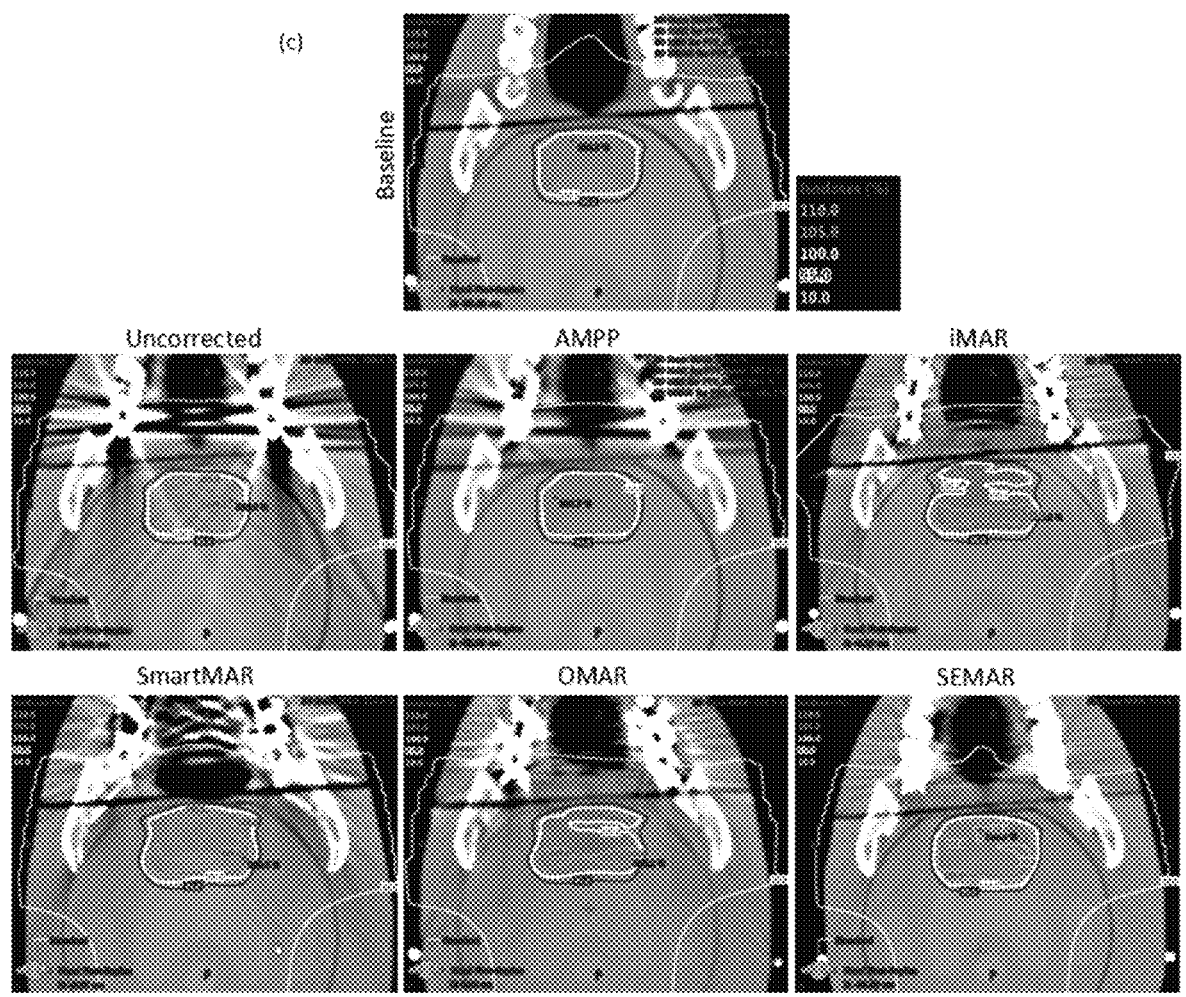

The proton dose distributions of the horseshoe, sphere, and bean targets can be seen in FIG. 16. The changes in dose distribution that were observed throughout the different targets were affected by the streaking artifacts, as shown on a representative CT slice. The same axial slice was selected in each image set to allow for a direct comparison. For all targets, the dose distributions calculated on the MAR-corrected and -uncorrected images showed substantial discrepancies compared to the baseline. The horseshoe target showed the most stable dose distribution across all image sets, with only a few hot and cold spots and reasonable target coverage compared to the baseline. In contrast, the sphere target showed all-around underdosing for all commercial MAR solutions and the uncorrected image. Conversely, the bean target showed a substantial increase in hotspots, with sometimes nearly the entire target covered by the 105% isodose line with SmartMAR and SEMAR. Alternatively, dose distributions copied onto AMPP-corrected images showed good agreement with the baseline across all targets analyzed.

Figure 17:
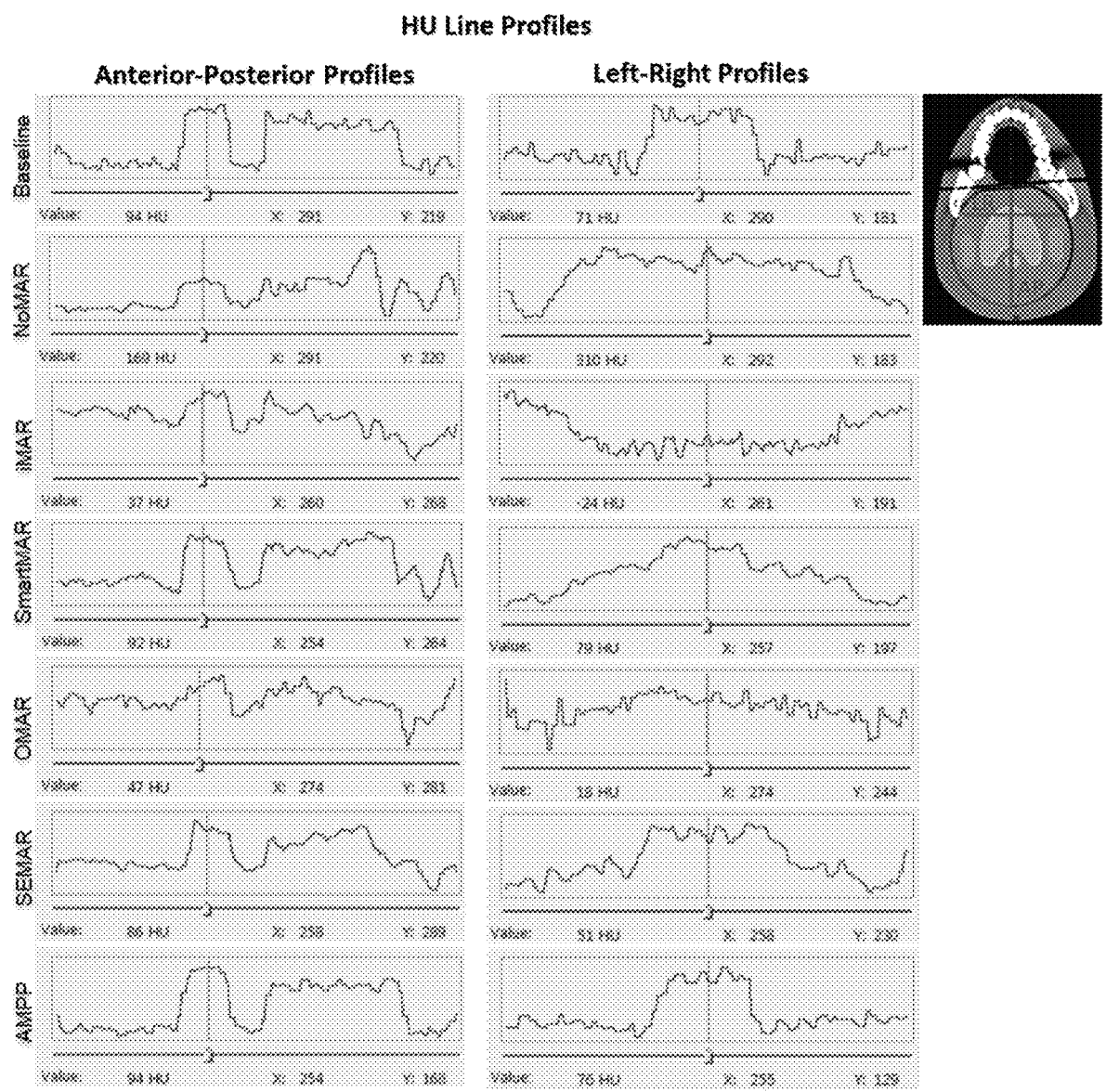
FIG. 17 displays AP and LR HU profiles extracted from each MAR-corrected and -uncorrected image set.

To further understand cases in which inadequate or inaccurate HU corrections were obtained with commercial MAR algorithms (corrections that were sometimes worse than no correction at all), we performed an HU profile assessment and an additional dosimetric investigation. Anterior-posterior (AP) and left-right (LR) HU profiles were extracted using the planning system from all image sets and are shown in FIG. 17. The blue vertical line serves as a reference point along the profiles and was kept consistent within the phantom, presenting the HU value inside the spinal cord on the AP profile and inside the horseshoe target on the LR profile. The figure demonstrates the substantial impact of uncorrected or commercially corrected algorithms in the HUs on the reference values compared to the baseline (37 HU to 169 HU and −24 HU to 310 HU for the AP and LR profiles, respectively, compared to 94 HU and 71 HU for the baseline). These results represent stopping power percentage differences of −4.4% to 2.7% and −7.1% to 10% compared to the baseline for the AP and LR profiles, respectively, and explain the proton beam range and dosimetric consequences seen in the treatment planning results (FIGS. 16 and 17).

In addition to the reference value varying substantially, the shape of the profile was drastically changed in some instances. The LR profile, for example, lost the baseline peak that represented the horseshoe target on the uncorrected, iMAR, SmartMAR, and OMAR image sets. In contrast to uncorrected or commercially corrected image profiles, AMPP profiles showed nearly identical reference HU values and had the most consistent shape compared to the baseline in both directions. This finding supports the dosimetry results that proton plans on AMPP-corrected images were the most similar to the baseline.

Figure 18:
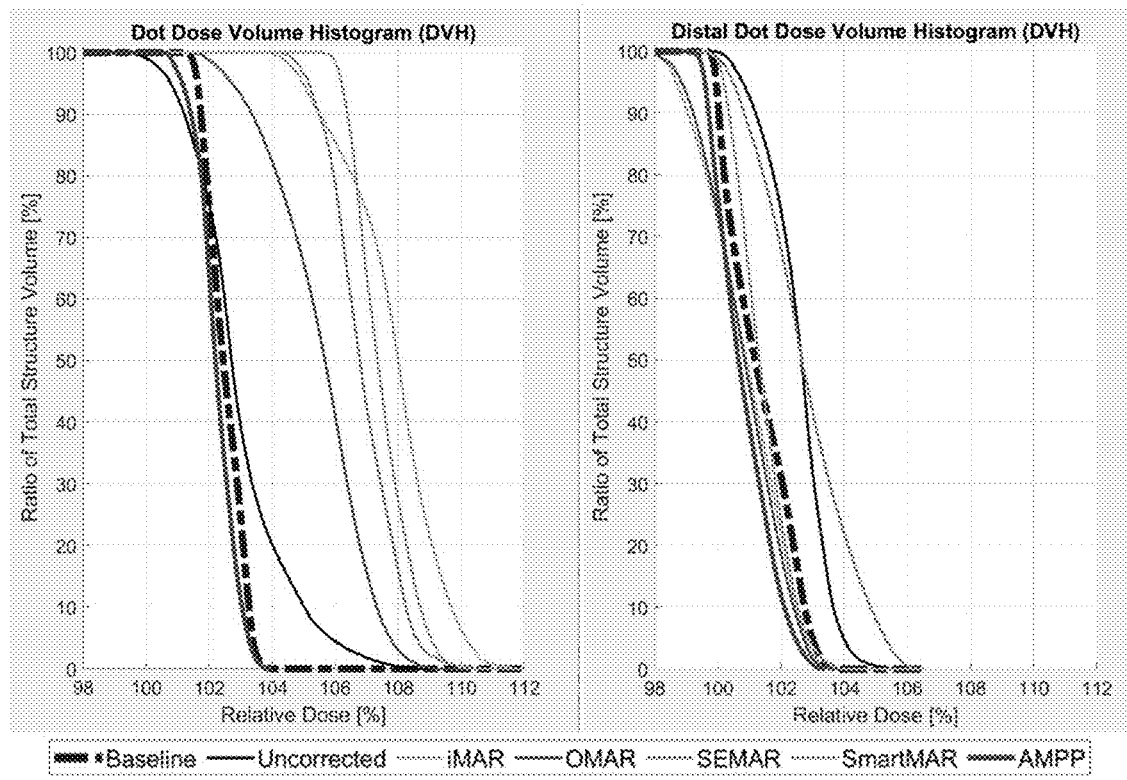
FIG. 18 displays a DVH comparison between the dot target in its original position and the dot target in the area with less severe metal artifacts. The commercial algorithms provide target coverages that are closer to the baseline once the target is moved to a location with fewer artifacts, indicating that success in artifact correction is related to the location within the phantom.

To further analyze algorithm performance, we repeated the treatment planning exercise for the dot target at a location that was originally less affected by artifacts (3 cm posteriorly). We then determined whether the differences seen were the result of the target size or target location. After moving the dot PTV, we found that the plans designed on the commercial algorithm image sets had improved performance, as they more closely matched the baseline DVH (FIG. 18). This finding supports the interpretation that commercial algorithms perform better when metal artifacts are minimal, indicating that their correction in severe artifact regions is insufficient.

4. DISCUSSION

Our study demonstrated that uncorrected CT metal artifacts and commercial MAR algorithms negatively affected proton dose distributions in all five target shapes and locations. The AMPP-corrected images, however, provided dose distributions that were consistently in agreement with the baseline dose distributions, as evidenced in FIG. 15.

None of the commercial MAR algorithms affected the dose distributions in a consistent manner. For instance, the Philips (OMAR) and Siemens (iMAR) solutions were both found to overdose the horseshoe target, underdose the sphere target, and simultaneously underdose (dip in the shoulder region of the target DVH) and overdose (increase in hotspots shown by the larger DVH tail and elevated D0.03 cc value) the bean target. In general, the dose distributions on the MAR-corrected and -uncorrected image sets underdosed the sphere target, overdosed the bean target, and had mixed results for the horseshoe target. It is also important to note that in some instances, the uncorrected (i.e., full artifact) image set yielded dose distributions that matched the baseline better than did the commercially corrected image sets. For instance, SmartMAR, iMAR, and OMAR on the sphere target and SEMAR and SmartMAR on the bean target showed DVH curves that agreed less well with the baseline plan than did the uncorrected image set.

The resulting dose distribution differences noted above between the baseline images and the uncorrected, commercial MAR algorithm-corrected, and AMPP algorithm-corrected images can be further understood in terms of the DVH metrics extracted from all of the proton plans. The CTV coverage provided by the AMPP-corrected image set was consistently the closest to the baseline for all targets analyzed, whereas no clear pattern of agreement was observed for the commercial MAR solutions. For example, the iMAR-corrected plan showed underdosing of the bean CTV (D99) but substantial overdosing of the dot CTV (D99).

With regards to volume coverage, the sphere target showed clinically unacceptable (V100>95) V100 results from OMAR, iMAR, SmartMAR, and uncorrected images, while AMPP showed identical coverage to the baseline plan. For the dot, horseshoe, and bean targets, several V100 values were 100% because the targets were substantially overdosed rather than because the artifacts were well managed by the MAR algorithm. The overdosing and creation of hotspots in the target are further illustrated through the D0.03 cc DVH metric. For those same targets (dot, bean and horseshoe), the MAR techniques that showed 100% V100s also showed the largest D0.03 cc values (underlined for clarity in Table 3).

This same overdosing was not observed for the sphere target because it was mostly underdosed; it tended to show mixed results in terms of dose coverage between the baseline results and other plans. In addition, no consistent performance was observed between the commercial algorithms for target heterogeneity. On the other hand, our in-house stereoscopic artifact management algorithm, AMPP, was in excellent agreement with the baseline metrics, as shown in Table 3.

A qualitative comparison of the dose distributions further demonstrated what was observed in the extracted DVH curves and planning metrics. The horseshoe target showed no major differences in the various dose distributions for the MAR corrections compared to the baseline, except for a few cold spots inside the target for the uncorrected and SEMAR plans. The sphere target, on the other hand, showed cold spots inside the PTV for all of the plans originating from the commercial MAR solution and uncorrected image sets, consistent with the DVH data. Alternatively, the bean target isodose lines showed several hotspots for all commercial techniques and cold spots in some instances (iMAR and OMAR). In contrast to the largely poor performances of the commercial MAR algorithms analyzed here, AMPP consistently showed dose distributions that overlaid the baseline dose distributions for all of the targets.

The results of dosimetry evaluations of the ideal baseline image set and the various MAR-corrected image sets suggest that commercial MAR algorithms' performance varies more with target location and less with target shape. The targets that were located close to the oral cavity and were therefore subject to more severe artifacts had dose distributions showing greater variations (the bean, sphere, and dot targets were located near the dental fillings in areas that traversed very light and very dark streaks). This is most likely the result of the inadequate HU correction obtained with the commercial MAR algorithms, which was sometimes worse than no correction at all.

A possible explanation for why AMPP consistently outperformed the commercial MAR algorithms is the image reconstruction process of the techniques. The majority of currently available commercial approaches are sinogram based and manipulate raw projection data through the identification, deletion, and replacement of corrupted raw data. The imprecise estimation of the removed data can assign incorrect HU values and create additional artifacts and blurring in the final images.[10, 11] Studies in the literature have also shown that these MAR approaches are generally not successful at reducing the artifacts created by dental fillings.[15] The HN region exhibits a complex geometry, with a large number of sharp transitions between the diverse types of tissues present (e.g., bone, organ types, and air). In contrast, AMPP does not require the replacement of deleted metal thresholded data with artificially interpolated data. Instead, it uses a stereoscopic solution to assign accurate HU data obtained from gantry-tilted scans; these data are used to reconstruct a final image that is free of artifacts posterior to the oral cavity. In addition to improving the visualization of tissues posterior to the oral cavity, it results in accurate HU values, allowing for the improved proton dose calculations and distributions observed in this study.

5. CONCLUSIONS

In this study, we determined the effect of major commercial MAR algorithms (GE, Siemens, Philips, and Canon) and a novel in-house stereoscopic technique developed using CT gantry tilts (AMPP) on proton therapy dose distributions using a realistic HN anthropomorphic phantom. CT metal artifacts negatively affected proton dose distributions on all five targets that were analyzed. The commercial MAR algorithm solutions examined here performed inconsistently among all targets compared to the metal-free baseline. A lack of CTV coverage and an increased number of hotspots were observed throughout all commercial solutions. Dose distribution errors were related to proximity to the artifacts, demonstrating the inability of commercial techniques to adequately correct severe artifacts. In contrast, AMPP consistently showed dose distributions that best matched the baseline for all five targets. This is likely because AMPP makes use of accurate HU information, as opposed to interpolated data as in commercial algorithms. Future work is planned to expand the proton dosimetry investigation performed here to HN patients in an IRB-approved study.

All of the devices, apparatus, systems and/or methods disclosed and claimed herein can be made and executed without undue experimentation in light of the present disclosure. While the devices, apparatus, systems and methods of this invention have been described in terms of particular embodiments, it will be apparent to those of skill in the art that variations may be applied to the devices, apparatus, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
1. Herman, G. T., *Correction for beam hardening in computed tomography*. Physics in Medicine & Biology, 1977. 24(1).
2. O'Daniel, J. C., et al., *The Effect of Dental Artifacts, Contrast Media, and Experience on Interobserver Contouring Variations in Head and Neck Anatomy*. American Journal of Clinical Oncology, 2007. 30(2): p. 191-198.
3. Kim, Y., et al., *The impact of dental metal artifacts on head and neck IMRT dose distributions*. Radiotherapy and Oncology, 2006. 79(2): p. 198-202.
4. Mail, N., et al., *The impacts of dental filling materials on RapidArc treatment planning and dose delivery: Challenges and solution*. Medical Physics, 2013.40(8): p. 081714-n/a.
5. Huang, J. Y., et al., *Approaches to reducing photon dose calculation errors near metal implants*. Medical Physics, 2016. 43(9): p. 5117-5130.
6. Schaffner, B. and E. Pedroni, *The precision of proton range calculations in proton radiotherapy treatment planning: experimental verification of the relation between CT-HU and proton stopping power*. Physics in Medicine and Biology, 1998. 43.
7. Jessie, Y. H., et al., *An evaluation of three commercially available metal artifact reduction methods for CT imaging*. Physics in Medicine & Biology, 2015. 60(3): p. 1047.
8. Ge, W., et al., *Iterative deblurring for CT metal artifact reduction*. IEEE Transactions on Medical Imaging, 1996. 15(5): p. 657-664.
9. Zhao, S., et al., *X-ray CT metal artifact reduction using wavelets: an application for imaging total hip prostheses*. IEEE Transactions on Medical Imaging, 2000. 19(12): p. 1238-1247.
10. Man, B. D., et al., *An iterative maximum-likelihood polychromatic algorithm for CT*. IEEE Transactions on Medical Imaging, 2001. 20(10): p. 999-1008.
11. Newhauser, W. D., et al., *Can megavoltage computed tomography reduce proton range uncertainties in treatment plans for patients with large metal implants?* Physics in medicine and biology, 2008. 53(9): p. 2327-2344.
12. Richard, P., et al., *Dental amalgam artifact: Adverse impact on tumor visualization and proton beam treatment planning in oral and oropharyngeal cancers*. Practical Radiation Oncology, 2015. 5(6): p. e583-e588.
13. Kalender, W. A., R. Hebel, and J. Ebersberger, *Reduction of CT artifacts caused by metallic implants*. Radiology, 1987. 164(2): p. 576-577.
14. Gjestby, L. et al. *Metal Artifact Reduction in CT: Where Are We After Four Decades?* IEEE Access, 2016. 10.1109/ACCESS.2016.2608621

U.S. Pat. No. 7,548,604
U.S. Pat. No. 7,818,045
U.S. Pat. No. 8,244,016
U.S. Pat. No. 8,254,518
U.S. Pat. No. 8,396,275
U.S. Pat. No. 8,891,847
U.S. Pat. No. 9,084,888
U.S. Pat. No. 9,437,018
U.S. Pat. No. 9,689,812
U.S. Ser. No. 10/147,207
U.S. Ser. No. 10/226,221
U.S. Ser. No. 10/265,044
U.S. Ser. No. 10/307,129
US 20060020200
US 20170238897

EXAMPLE 1 REFERENCES

1. Schauer D A, Linton O W (2009) NCRP report no. 160, ionizing radiation exposure of the population of the United States, medical exposure—are we doing less with more, and is there a role for health physicists? Health Phys 97:1-5.
2. O'Daniel J C, Rosenthal D I, Garden A S, et al (2007) The effect of dental artifacts, contrast media, and experience on interobserver contouring variations in head and neck anatomy. Am J Clin Oncol 30:191-198.
3. Kim Y, Tome W A, Bal M, McNutt T R, Spies L (2006) The impact of dental metal artifacts on head and neck IMRT dose distributions. Radiother Oncol 79:198-202.
4. Mail N, Albarakati Y, Ahmad Kahn M, et al (2013) The impacts of dental filling materials on RapidArc treatment planning and dose delivery: challenges and solution. Med Phys 40:081714.
5. Huang J Y, Followill D S, Howell R M, et al (2016) Approaches to reducing photon dose calculation errors near metal implants. Med Phys 43:5117-5130.
6. Zhao S, Robertson D, Wang G, Whiting B, Bae T (2000) X-ray CT metal artifact reduction using wavelets: an application for imaging total hip prostheses. IEEE Trans Med Imaging 19:1238-1247.
7. Man B, Nuyts J, Dupont P, Marchal G, Suetens P (2001) An iterative maximum-likelihood polychromatic algorithm for CT. IEEE Trans Med Imaging 20:999-1008.
8. Yazdia M, Gingras L, Beaulieu L (2005) An adaptive approach to metal artifact reduction in helical computed tomography for radiation therapy treatment planning: Experimental and clinical studies. Int J Radiat Oncol Biol Phys 62:1224-1231.

9. Zhang X, Wang J, Xing L (2011) Metal artifact reduction in x-ray computed tomography (CT) by constrained optimization. Med Phys 38:701-711.
10. Meyer E, Raupach R, Lell M, Schmidt B, Kachelrie M (2010) Normalized metal artifact reduction (NMAR) in computed tomography. Med Phys 37:5482-5493.
11. Li H, Noel C, Chen H, et al (2012) Clinical evaluation of a commercial orthopedic metal artifact reduction tool for CT simulations in radiation therapy. Med Phys 39:7507-7517.
12. Axente M, Paidi A, Von E, et al (2015) Clinical evaluation of the iterative metal artifact reduction algorithm for CT simulation in radiotherapy. Med Phys 42:1170-1183
13. GE Healthcare (2013) Smart metal artifact reduction (MAR) white paper.
14. Toshiba Medical. Single energy metal artifact reduction white paper.
15. Huang J. Kerns J, Nute J, et al (2015) An evaluation of three commercially available metal artifact reduction methods for CT imaging. Phys Med Biol 60:1047-1067.
16. Das I, Paganetti H (2015) Principles and Practice of Proton Beam Therapy.
17. Grant R, Summers P, Neihart, J, et al (2014) Relative stopping power measurements to aid in the design of anthropomorphic phantoms for proton radiotherapy. J Appl Clin Med Phys 15:4523.
18. Molineu A, Hernandez N, Nguyen T (2013) Credentialing results from IMRT irradiations of an anthropomorphic head and neck phantom. Med Phys 40: 022101.
19. Branco D, Taylor P, Zhang X (2017) An Anthropomorphic Head and Neck Quality Assurance Phantom for Credentialing of Intensity-Modulated Proton Therapy. Int J Particle Ther 4:40:47

EXAMPLE 2 REFERENCES

1. O'Daniel C, Rosenthal I, Garden S, et al. The effect of dental artifacts, contrast media, and experience on interobserver contouring variations in head and neck anatomy. *J Appl Clin Med Phys.* 2007; 30(2):191-198.
2. Kim Y, Tomé W, Bal M, McNutt T, Spies L. The impact of dental metal artifacts on head and neck IMRT dose distributions. Radiother and Oncol. 2006; 79(2): 198-202.
3. Mail N, Albarakati Y, Ahmad Khan M, et al. The impacts of dental filling materials on RapidArc treatment planning and dose delivery: Challenges and solution. *Med Phys.* 2013; 40(8): 817141-8171411.
4. Herman G. Correction for beam hardening in computed tomography. *Phys Med Bio.* 1979; 24(1): 81.
5. Lifeng Y, Hua L, Jan M, et al. Metal artifact reduction from reformatted projections for hip prostheses in multislice helical computed tomography: techniques and initial clinical results. *Invest Radiol.* 2009; 44(11): 691-696.
6. Kalender W, Hebel R, Ebersberger J. Reduction of CT artifacts caused by metallic implants. *Radiol.* 1987; 164 (2): 576-577.
7. Meyer E, Raupach R, Lell M, Schmidt B, Kachelriess M. Normalized metal artifact reduction (NMAR) in computed tomography. *Med Phys.* 2010; 37(10): 5482-5493.
8. Bal M, Spies L. Metal artifact reduction in CT using tissue-class modeling and adaptive prefiltering. *Med Phys.* 2006; 33(8): 2852-2859.
9. Branco D, Kry S, Taylor P, et al. A stereoscopic CT artifact reduction method image quality comparison to current vendor solutions. *Conference Proceedings.* ESTRO 2020.
10. Subhas N, Primak A, Obuchowski N, et al. Iterative metal artifact reduction: Evaluation and optimization of technique. *Skeletal Radiol.* 2014; 43(12): 1729-1735.
11. Zhang, D. Single Energy Metal Artifact Reduction A Reliable Metal Management Tool in CT. 2017. White Paper.
12. Li H, Noel C, Chen H, et al. Clinical evaluation of a commercial orthopedic metal artifact reduction tool for CT simulations in radiation therapy. *Med Phys.* 2012; 39(12): 7507-7517.
13. Mahnken A, Raupach R, Wildberger J, et al., A new algorithm for metal artifact reduction in computed tomography: in vitro and in vivo evaluation after total hip replacement. Invest *Radiol.* 2003; 38(12): 769-775.
14. Verburg J, J Seco. CT metal artifact reduction method correcting for beam hardening and missing projections. *Phys Med Bio.* 2012; 57(9): 2803-2818.
15. Huang J, Kerns J, Nute J, et al. An evaluation of three commercially available metal artifact reduction methods for CT imaging. *Phys Med Bio.* 2015; 60(3): 1047-1067.
16. Huang J, Followill D, Howell R, et al., Approaches to reducing photon dose calculation errors near metal implants. *Med Phys.* 2016; 43(9): 5117-5130.
17. Wei J, Sandison G, Hsi W, et al. Dosimetric impact of a CT metal artefact suppression algorithm for proton, electron and photon therapies. *Phys Med Bio.* 2006; 51(20): 5183-5197.
18. Paganetti H. Range uncertainties in proton therapy and the role of Monte Carlo simulations. *Phys Med Bio.* 2012; 57(11): 99-117.
19. Branco D, Kry S, Taylor P, et al. Development of a stereoscopic CT metal artifact management algorithm using gantry angle tilts for head and neck patients. *J Appl Clin Med Phys.* 2019. Accepted/Pending Publication.
20. Grant R, Summers P, Neihart J, et al. Relative stopping power measurements to aid in the design of anthropomorphic phantoms for proton radiotherapy. *J Appl Clin Med Phys.* 2014; 15(2): 4523.
21. Lewis D, Taylor P, Followill D, et al. A New Anthropomorphic Pediatric Spine Phantom for Proton Therapy Clinical Trial Credentialing. *Int J Part Ther.* 2018; 4(4): 20-27.
22. Branco D, Taylor P, Zhang X, et al. An Anthropomorphic Head and Neck Quality Assurance Phantom for Credentialing of Intensity-Modulated Proton Therapy. *Int J Part Ther.* 2017; 4(3): 40-47.

The invention claimed is:
1. A method of imaging a region of a subject comprising an artifact, the method comprising:
obtaining a first computed tomography (CT) scan of the region, wherein the first CT scan comprises a first set of images obtained at a superior angle with respect to the subject;
obtaining a second CT scan of the region, wherein the second CT scan comprises a second set of images obtained at an inferior angle with respect to the subject;
performing a first three-dimensional affine geometric transformation to the first set of images and to the second set of images;
performing a second three-dimensional affine geometric transformation to the first set of images and to the second set of images;
converting the first set of images to a first modified set of axial images, wherein a first portion of the first modified set of axial images comprises a first artifact-free region posterior to the artifact;

converting the second set of images to a second modified set of axial images, wherein a second portion of the second modified set of axial images comprises a second artifact-free region posterior to the artifact; and constructing an image of a region posterior to the artifact by combining the first artifact-free region posterior to the artifact and the second artifact-free region posterior to the artifact.

2. The method of claim 1 wherein the first three-dimensional affine geometric transformation is a shear transformation applied on a sagittal plane of the first set of images and the second set of images.

3. The method of claim 2 wherein the second three-dimensional affine geometric transformation is geometrical correction transformation of the first set of images and the second set of images.

4. The method of claim 1 wherein the first CT scan and the second CT scan are obtained by tilting a gantry of a CT scanner.

5. The method of claim 1 wherein constructing the image of the region posterior to the artifact comprises combining the first artifact-free region posterior to the artifact and the second artifact-free region posterior to the artifact comprises analyzing pixels in the first modified set of axial images for a threshold Hounsfield Unit (HU) value.

6. The method of claim 5 wherein constructing the image of the region posterior to the artifact comprises combining the first artifact-free region posterior to the artifact and the second artifact-free region posterior to the artifact comprises analyzing pixels in the second modified set of axial images for the threshold HU value.

7. The method of claim 6 wherein the threshold HU value is equivalent to an HU value for a metal.

8. The method of claim 7 wherein the metal is an amalgam dental filling.

9. The method of claim 7 wherein the metal is stainless steel.

10. An apparatus for imaging a region of a subject comprising an artifact, the apparatus comprising:
a computed tomography (CT) scanner comprising support surface and a tiltable gantry, wherein the CT scanner is configured to obtain CT scans at a superior and an inferior angle to the support surface;
a computer processor; and
a computer-readable medium which comprises instructions that when executed by the computer processor will cause the apparatus to perform the following steps:
obtain a first CT scan of a region of a subject comprising an artifact, wherein the first CT scan comprises a first set of images obtained at a superior angle with respect to the subject;
obtain a second CT scan of the region, wherein the second CT scan comprises a second set of images obtained at an inferior angle with respect to the subject;
perform a first three-dimensional affine geometric transformation to the first set of images and to the second set of images;
perform a second three-dimensional affine geometric transformation to the first set of images and to the second set of images;
convert the first set of images to a first modified set of axial images, wherein a first portion of the first modified set of axial images comprises a first artifact-free region posterior to the artifact;
convert the second set of images to a second modified set of axial images, wherein a second portion of the second modified set of axial images comprises a second artifact-free region posterior to the artifact; and
construct an image of a region posterior to the artifact by combining the first artifact-free region posterior to the artifact and the second artifact-free region posterior to the artifact.

* * * * *